United States Patent
Calderon Oliveras et al.

(10) Patent No.: US 11,554,226 B2
(45) Date of Patent: Jan. 17, 2023

(54) DRUG DELIVERY DEVICE WITH ELECTRONICS

(71) Applicant: Norton (Waterford) Limited, Waterford (IE)

(72) Inventors: Enrique Calderon Oliveras, Barcelona (ES); Daniel Buck, Waterford (IE)

(73) Assignee: Norton (Waterford) Limited, Waterford (IE)

( * ) Notice: Subject to any disclaimer, the term of this patent is extended or adjusted under 35 U.S.C. 154(b) by 0 days.

(21) Appl. No.: 16/875,282

(22) Filed: May 15, 2020

(65) Prior Publication Data
US 2020/0360630 A1    Nov. 19, 2020

Related U.S. Application Data

(60) Provisional application No. 62/849,552, filed on May 17, 2019.

(51) Int. Cl.
| | | |
|---|---|---|
| *A61M 15/00* | (2006.01) | |
| *G16H 40/40* | (2018.01) | |
| *G16H 20/13* | (2018.01) | |

(52) U.S. Cl.
CPC ...... *A61M 15/007* (2014.02); *A61M 15/0021* (2014.02); *G16H 20/13* (2018.01);
(Continued)

(58) Field of Classification Search
CPC .......... A61M 15/0023; A61M 15/0025; A61M 15/0026; A61M 15/0091; A61M 2205/33;
(Continued)

(56) References Cited

U.S. PATENT DOCUMENTS

| | | |
|---|---|---|
| 955,201 A | 4/1910 | Rand |
| 4,984,158 A | 1/1991 | Hillsman |
| (Continued) | | |

FOREIGN PATENT DOCUMENTS

| | | |
|---|---|---|
| EP | 667168 A1 | 8/1995 |
| EP | 1135056 B1 | 8/2006 |
| (Continued) | | |

OTHER PUBLICATIONS

Minnesota Department of Health: "Asthma Medications", URL:https://www.health.state.mn.us/diseases/asthma/medications/images/MedsPoster2sided14x13.pdf, Mar. 2017, 2 pages.

*Primary Examiner* — Justine R Yu
*Assistant Examiner* — Matthew R Moon
(74) *Attorney, Agent, or Firm* — Flaster Greenberg, P.C.

(57) ABSTRACT

A system may include an external device and an inhaler. The external device may include a processor, a communication circuit, and memory. The inhaler may include a mouthpiece, medicament, a mechanical dose counter, and an electronics module comprising a processor and a communication circuit. The electronics module may record a dosing event when the inhaler is actuated, such as when the mouthpiece cover is opened, and send a signal indicating the dosing event to the external device. The external device may receive a mechanical dose reading of the mechanical dose counter, determine an electronic dose reading based on the signal indicating the dosing event, determine that a discrepancy between the mechanical dose reading and the electronic dose reading exceeds a threshold, and notify the user of the discrepancy, for example, by providing a notification to the user by way of a mobile application residing on the external device.

20 Claims, 12 Drawing Sheets

(52) U.S. Cl.
CPC ......... *G16H 40/40* (2018.01); *A61M 2205/18* (2013.01); *A61M 2205/3553* (2013.01); *A61M 2205/50* (2013.01)

(58) Field of Classification Search
CPC ...... A61M 2205/35; A61M 2205/3546; A61M 2205/3569; A61M 2205/3576; A61M 2205/3584; A61M 2205/3592; A61M 15/007; A61M 15/0071; A61M 15/0073; A61M 15/0075; A61M 15/0078; A61M 15/008; G01L 27/00; G01N 33/0006; G01N 33/007
USPC .............................................. 222/25, 30, 36
See application file for complete search history.

(56) References Cited

U.S. PATENT DOCUMENTS

| | | | |
|---|---|---|---|
| 5,020,527 A * | 6/1991 | Dessertine | A61M 15/0065 128/200.14 |
| 5,071,453 A | 12/1991 | Hradek et al. | |
| 5,363,842 A | 11/1994 | Mishelevich et al. | |
| 5,505,192 A | 4/1996 | Samiotes et al. | |
| 5,779,122 A | 7/1998 | Martinelli | |
| 5,809,997 A | 9/1998 | Wolf et al. | |
| 5,839,429 A | 11/1998 | Marnfeldt et al. | |
| 5,842,468 A | 12/1998 | Denyer et al. | |
| 5,887,586 A | 3/1999 | Dahlbaeck et al. | |
| 6,285,731 B1 | 9/2001 | Marnfeldt et al. | |
| 6,302,292 B1 * | 10/2001 | Schafer | G07F 9/02 221/2 |
| 6,390,088 B1 | 5/2002 | Noehl et al. | |
| 6,446,627 B1 | 9/2002 | Bowman et al. | |
| 6,932,083 B2 | 8/2005 | Jones et al. | |
| 6,958,691 B1 | 10/2005 | Robertson et al. | |
| 6,978,780 B1 | 12/2005 | Marnfeldt et al. | |
| 6,990,975 B1 | 1/2006 | Jones et al. | |
| 7,072,738 B2 | 7/2006 | Robertson et al. | |
| 7,151,456 B2 | 12/2006 | Godfrey et al. | |
| 7,191,777 B2 | 3/2007 | Brand et al. | |
| 7,198,172 B2 | 4/2007 | Harvey et al. | |
| 7,233,228 B2 | 6/2007 | Lintell | |
| 7,249,687 B2 | 7/2007 | Anderson | |
| 7,347,200 B2 | 3/2008 | Jones et al. | |
| 7,383,837 B2 | 6/2008 | Robertson et al. | |
| 7,424,888 B2 | 9/2008 | Harvey et al. | |
| 7,495,546 B2 | 2/2009 | Lintell | |
| 7,587,988 B2 | 9/2009 | Bowman et al. | |
| 7,837,648 B2 | 11/2010 | Blair et al. | |
| 8,201,556 B2 | 6/2012 | Jones et al. | |
| 8,231,573 B2 | 7/2012 | Edwards et al. | |
| 8,240,301 B2 | 8/2012 | Spaargaren et al. | |
| 8,424,517 B2 | 4/2013 | Sutherland et al. | |
| 8,464,707 B2 | 6/2013 | Jongejan et al. | |
| 8,511,304 B2 | 8/2013 | Anderson et al. | |
| 8,539,945 B2 * | 9/2013 | Solomon | G16H 50/30 128/200.23 |
| 8,547,239 B2 | 10/2013 | Peatfield et al. | |
| 8,807,131 B1 | 8/2014 | Chan et al. | |
| 8,960,189 B2 | 2/2015 | Morrison | |
| 8,978,966 B2 | 3/2015 | Walsh et al. | |
| 8,997,735 B2 | 4/2015 | Zierenberg et al. | |
| 9,056,174 B2 | 6/2015 | Bradshaw et al. | |
| 9,174,009 B2 | 11/2015 | Peatfield et al. | |
| 9,188,579 B2 | 11/2015 | Shen et al. | |
| 9,242,056 B2 | 1/2016 | Andersen et al. | |
| 9,339,616 B2 | 5/2016 | Denny et al. | |
| 9,364,619 B2 | 6/2016 | Polidoro et al. | |
| 9,427,534 B2 | 8/2016 | Bruin et al. | |
| 9,463,291 B2 | 10/2016 | Imran | |
| 9,468,729 B2 | 10/2016 | Sutherland et al. | |
| 9,550,031 B2 | 1/2017 | Van Sickle et al. | |
| 9,555,201 B2 | 1/2017 | Collins et al. | |
| 9,694,147 B2 | 7/2017 | Peatfield et al. | |
| 9,736,642 B2 | 8/2017 | Ostrander et al. | |
| 9,839,398 B2 | 12/2017 | Yamamori et al. | |
| 9,872,964 B2 | 1/2018 | Cline et al. | |
| 9,911,308 B2 | 3/2018 | Edwards et al. | |
| 9,943,656 B2 | 4/2018 | Shears et al. | |
| 9,956,360 B2 | 5/2018 | Germinario et al. | |
| 9,962,507 B2 | 5/2018 | Germinario et al. | |
| 9,962,508 B2 | 5/2018 | Bruin et al. | |
| 10,016,134 B2 | 7/2018 | Hansen et al. | |
| 10,046,121 B2 | 8/2018 | Kolb et al. | |
| 10,300,227 B2 | 5/2019 | Sutherland et al. | |
| 10,369,305 B2 | 8/2019 | Li et al. | |
| 10,406,305 B2 | 9/2019 | Collins et al. | |
| 10,449,310 B2 | 10/2019 | Jackson et al. | |
| 10,668,232 B2 | 6/2020 | Sutherland et al. | |
| 10,729,861 B2 | 8/2020 | Turner et al. | |
| 2002/0185128 A1 | 12/2002 | Theobald et al. | |
| 2003/0192535 A1 | 10/2003 | Christrup et al. | |
| 2003/0205229 A1 | 11/2003 | Crockford et al. | |
| 2004/0089299 A1 | 5/2004 | Bonney et al. | |
| 2004/0117062 A1 | 6/2004 | Bonney et al. | |
| 2005/0043674 A1 | 2/2005 | Blair et al. | |
| 2005/0119604 A1 | 6/2005 | Bonney et al. | |
| 2005/0161467 A1 | 7/2005 | Jones | |
| 2005/0247312 A1 | 11/2005 | Davies | |
| 2005/0251289 A1 | 11/2005 | Bonney et al. | |
| 2006/0254581 A1 | 11/2006 | Genova et al. | |
| 2007/0017506 A1 | 1/2007 | Bell et al. | |
| 2007/0251950 A1 | 11/2007 | Bacon | |
| 2007/0295329 A1 | 12/2007 | Lieberman et al. | |
| 2008/0017190 A1 * | 1/2008 | Anandampillai | A61M 15/007 128/200.23 |
| 2008/0173301 A1 * | 7/2008 | Deaton | A61M 15/0091 128/203.12 |
| 2008/0178872 A1 | 7/2008 | Genova et al. | |
| 2008/0230057 A1 | 9/2008 | Sutherland et al. | |
| 2009/0151718 A1 | 6/2009 | Hunter et al. | |
| 2009/0194104 A1 | 8/2009 | Van et al. | |
| 2009/0221308 A1 | 9/2009 | Lerner et al. | |
| 2010/0242960 A1 | 9/2010 | Zangerle et al. | |
| 2010/0250280 A1 | 9/2010 | Sutherland et al. | |
| 2011/0041845 A1 * | 2/2011 | Solomon | A61M 15/009 128/203.12 |
| 2011/0226242 A1 | 9/2011 | Von et al. | |
| 2011/0282693 A1 | 11/2011 | Craft | |
| 2011/0283997 A1 | 11/2011 | Walsh et al. | |
| 2012/0055472 A1 | 3/2012 | Brunnberg et al. | |
| 2012/0080029 A1 | 4/2012 | Koerner et al. | |
| 2013/0008436 A1 | 1/2013 | Von Hollen et al. | |
| 2013/0151162 A1 | 6/2013 | Harris et al. | |
| 2013/0239957 A1 | 9/2013 | Pinfold | |
| 2013/0269685 A1 | 10/2013 | Jung et al. | |
| 2013/0298905 A1 | 11/2013 | Levin et al. | |
| 2014/0106324 A1 | 4/2014 | Adams et al. | |
| 2014/0182584 A1 | 7/2014 | Sutherland et al. | |
| 2014/0264653 A1 | 9/2014 | Cheng et al. | |
| 2014/0305429 A1 | 10/2014 | Lewis | |
| 2015/0283341 A1 | 10/2015 | Adams et al. | |
| 2016/0045683 A1 * | 2/2016 | Cheatham, III | A61M 15/0071 128/203.14 |
| 2016/0082208 A1 * | 3/2016 | Ballam | A61M 16/024 128/200.14 |
| 2016/0128389 A1 | 5/2016 | Lamb et al. | |
| 2016/0144141 A1 | 5/2016 | Sabharwal et al. | |
| 2016/0166766 A1 | 6/2016 | Schuster et al. | |
| 2016/0166783 A1 | 6/2016 | Kohnle et al. | |
| 2016/0228657 A1 | 8/2016 | Sutherland | |
| 2016/0256639 A1 | 9/2016 | Van Sickle et al. | |
| 2016/0303336 A1 * | 10/2016 | Arp | A61K 9/0075 |
| 2016/0314256 A1 | 10/2016 | Su et al. | |
| 2016/0325057 A1 * | 11/2016 | Morrison | A61M 15/0065 |
| 2017/0014583 A1 | 1/2017 | Koerner | |
| 2017/0079557 A1 | 3/2017 | Lauk | |
| 2017/0109493 A1 | 4/2017 | Hogg et al. | |
| 2017/0140125 A1 | 5/2017 | Hogg et al. | |
| 2017/0164892 A1 | 6/2017 | Sezan et al. | |
| 2017/0173279 A1 | 6/2017 | Sutherland et al. | |
| 2017/0246406 A1 | 8/2017 | Sutherland | |
| 2017/0258993 A1 | 9/2017 | Pizzochero et al. | |

(56) References Cited

U.S. PATENT DOCUMENTS

| | | |
|---|---|---|
| 2017/0262613 A1 | 9/2017 | Ljungberg |
| 2017/0274163 A1* | 9/2017 | Oliveras ................ G16H 40/63 |
| 2017/0325734 A1 | 11/2017 | Sutherland et al. |
| 2017/0363673 A1 | 12/2017 | Mukherjee |
| 2018/0011988 A1 | 1/2018 | Ziegler et al. |
| 2018/0052964 A1 | 2/2018 | Adelson |
| 2018/0085540 A1 | 3/2018 | Dantsker et al. |
| 2018/0125365 A1 | 5/2018 | Hunter et al. |
| 2018/0140078 A1 | 5/2018 | Calderon et al. |
| 2018/0140786 A1 | 5/2018 | Calderon Oliveras et al. |
| 2018/0140788 A1 | 5/2018 | Calderon Oliveras et al. |
| 2018/0161530 A1 | 6/2018 | Ganton et al. |
| 2018/0200460 A1 | 7/2018 | Ziegler et al. |
| 2018/0221600 A1 | 8/2018 | Shears et al. |
| 2018/0236187 A1* | 8/2018 | Jung .................. A61M 15/007 |
| 2018/0369514 A1 | 12/2018 | Adelson |
| 2019/0134322 A1 | 5/2019 | Fabien |
| 2019/0151577 A1 | 5/2019 | Jung et al. |
| 2019/0175850 A1 | 6/2019 | Petit |
| 2019/0298941 A1* | 10/2019 | Collins ............... A61M 15/002 |
| 2019/0307648 A1 | 10/2019 | Bartos |
| 2019/0328984 A1 | 10/2019 | Yang et al. |
| 2019/0385727 A1 | 12/2019 | Manice et al. |
| 2020/0061301 A1 | 2/2020 | Hatamian et al. |
| 2020/0061314 A1 | 2/2020 | Hatamian et al. |
| 2020/0147328 A1 | 5/2020 | Kulkarni et al. |

FOREIGN PATENT DOCUMENTS

| | | |
|---|---|---|
| EP | 1992381 A1 | 11/2008 |
| EP | 3228345 A1 | 10/2017 |
| JP | 2013516265 A | 5/2013 |
| WO | 9522365 A1 | 8/1995 |
| WO | 9963901 A1 | 12/1999 |
| WO | 9964095 A2 | 12/1999 |
| WO | 03063754 A1 | 8/2003 |
| WO | 2009003989 A1 | 1/2009 |
| WO | 2011083377 A1 | 7/2011 |
| WO | WO 2016/030521 A1 | 8/2015 |
| WO | 2016043601 A1 | 3/2016 |
| WO | WO 2016/030521 A1 | 3/2016 |
| WO | WO 2016/081294 A1 | 5/2016 |
| WO | 2017005605 A1 | 1/2017 |
| WO | 2017051389 A1 | 3/2017 |
| WO | WO 2017/174588 A1 | 4/2017 |
| WO | 2017129521 A1 | 8/2017 |
| WO | 2017141194 A1 | 8/2017 |
| WO | 2017176693 A1 | 10/2017 |
| WO | 2017176704 A1 | 10/2017 |
| WO | 2017180980 A1 | 10/2017 |
| WO | 2017189712 A1 | 11/2017 |
| WO | 2018091678 A1 | 5/2018 |
| WO | 2018128976 A1 | 7/2018 |
| WO | 2018134552 A1 | 7/2018 |
| WO | 2018134553 A1 | 7/2018 |
| WO | 2018175579 A1 | 9/2018 |
| WO | WO 2019/121386 A1 | 12/2018 |
| WO | WO 2019/180214 A1 | 3/2019 |
| WO | WO 2020/058823 A1 | 9/2019 |
| WO | WO 2020/182655 A1 | 9/2020 |

* cited by examiner

DRUG DELIVERY DEVICE WITH ELECTRONICS

CROSS-REFERENCE TO RELATED APPLICATIONS

This application claims the benefit of Provisional U.S. Patent Application No. 62/849,552, filed May 17, 2019, the disclosure of which is incorporated herein by reference in its entirety.

BACKGROUND

Drug delivery devices facilitate the delivery of medication into a patient's body via various routes of administration. Typical routes of administration include oral, topical, sublingual inhalation, injection, and the like. The devices may be used to deliver medications for the treatment various diseases, ailments, and medical conditions. Inhalation devices, for example, may be used to treat asthma, chronic obstructive pulmonary disease (COPD) and cystic fibrosis (CF). While drug delivery devices are designed to deliver an appropriate dose of medication to a patient as part of a therapeutic treatment, the effectiveness of a particular treatment may be influenced by non-physiological factors, such as the patient's adherence and compliance.

In the context of a drug therapy, adherence may refer to the degree to which a patient is following a prescribed dosing regimen. For example, if the patient's prescription calls for two doses each day, and the patient is taking two doses per day, the patient may be considered 100% adherent. If the patient is only taking one dose per day, he or she may be deemed only 50% adherent. In the latter case, the patient may not be receiving the treatment prescribed by his or her doctor, which may negatively affect the efficacy of the therapeutic treatment.

Compliance may refer to a patient's technique when using a particular drug delivery device. If the patient is using the device in a manner that is recommended by a doctor or by a manufacturer, the device is likely to deliver the desired dose of medication and the patient may be deemed compliant. However, if the device is not being used properly during drug administration, the device's ability to deliver a proper dose of medication may be compromised. As such, the patient may be deemed non-compliant. In the case of an inhalation device, for example, the patient may need to achieve a minimum inspiratory effort to ensure a full dose of medication is delivered from the device into the patient's lungs. For some patients, such as children and the elderly, meeting the requirements for full compliance may be difficult due to physical limitations, such as limited lung function. Accordingly, like adherence, failing to achieve full compliance may reduce the effectiveness of a prescribed treatment.

A patient's ability to achieve full compliance may be further complicated by certain physical properties of the medication. For example, some respiratory medications may consist of fine particles and/or may lack any odor or taste. Thus, a patient using an inhalation device may not be able to correct a non-compliant use because he or she may not be able to immediately detect or sense that medication is being inhaled and/or know whether the amount of inhaled medication complies with the prescription.

SUMMARY

A system may include an external device and an inhalation device (e.g., an inhaler). The external device may include a processor, a communication circuit, and memory. The inhaler may include a mouthpiece, medicament, a mechanical dose counter, and an electronics module comprising a processor, a communication circuit, and a sensor configured to measure air flow through the inhaler (e.g., such as through a flow channel of the inhaler). The mechanical dose counter may decrement when a mouthpiece cover of the inhaler is moved from an open position to a closed position (e.g., to cover the mouthpiece). The sensor may, for example, include any combination of sensors, such as a pressure sensor, a temperature sensor, a humidity sensor, an acoustic sensor, an optical sensor, an orientation sensor, and/or the like. The pressure sensor may be configured to measure pressure changes (e.g., such as a pressure drop) through the inhaler. The acoustic sensor may be configured to measure air flowing past the acoustic sensor. The sensor may be configured to measure a frequency of a collision of a capsule with a capsule holder of the inhaler. The optical sensor may be configured to measure the passage of powder particles past the sensor.

The electronics module may record a dosing event when a mouthpiece cover of the inhaler is moved from the closed position to the open position to expose the mouthpiece to the user. The electronics module may be include a processor capable of performing the processing described herein. The electronics module may include a switch that is actuated when the mouthpiece cover of the inhaler is moved from the closed position to the open position. The switch may be used to change the electronics module between power states (e.g., between an off or sleep state and an active state). Alternatively or additionally, the electronics module may record a dosing event when feedback from the sensor exceeds a threshold (e.g., when a pressure measurement from a pressure sensor exceeds a threshold). For instance, in some examples, the electronics module (e.g., and/or a mobile application residing on the external device) may be configured to use the feedback from the sensor to validate a dosing event that is triggered based on the mouthpiece cover being moved from the closed position to the open position. For example, the electronics module may determine whether the feedback from the sensor indicates a good or fair inhalation, and if so, may use that determination to validate that the dosing event that is triggered back on the mouthpiece cover being moved from the closed position to the open position. The electronics module may be configured to send a signal indicating the dosing event to the external device (e.g., the signal may be an electronic dose reading (e.g., an accumulation of dosing events), the signal may include the dosing event (e.g., where the dosing event is based on actuation of a switch, based on inhalation parameters determined from sensor data exceeding a threshold, etc.), and/or the signal may be raw data from a sensor).

The external device may determine (e.g., receive) a mechanical dose reading of the mechanical dose counter. For example, the external device may use a camera of the external device to determine the mechanical dose reading (e.g., by prompting the user to take a picture of a mechanical dose counter or hold a camera of the external device over the mechanical dose counter), may prompt the user to manually input the mechanical dose reading into the external device (e.g., into a mobile application residing on the external device) to determine the mechanical dose reading, and/or may determine the mechanical dose reading through direct input by a technician (e.g., if the inhaler is returned, due to misuse or any other reason, to the vendor or their agent).

The external device may determine an electronic dose reading based on the signal indicating the dosing event. For example, the external device may increment the electronic dose reading for each signal indicating a dosing event that is received from the electronics module. Alternatively or additionally, the electronics module may determine the electronic dose reading based on recorded dosing events, and send the electronic dose reading to the external device.

The external device may determine that a discrepancy between the mechanical dose reading and the electronic dose reading exceeds a threshold, and notify the user, the vendor of the inhaler, and/or a health care provider (HCP) of the discrepancy. For example, the external device may notify the user of the discrepancy by providing a notification to the user by way of a mobile application residing on the external device, by illuminating one or more light emitting diodes (LEDs) of the inhaler, by outputting an audible signal through a speaker of the inhaler or external device, by sending a text, email, or instant message to the external device or DHP, and/or by providing a notification to the DHP.

An inhaler may include main body comprising a mouthpiece and a mouthpiece cover, medicament, and a sensor configured to measure air flow through the inhaler (e.g., such as through a flow channel of the inhaler). The sensor may, for example, include any combination of sensors, such as a pressure sensor, a temperature sensor, a humidity sensor, an acoustic sensor, an optical sensor, an orientation sensor, and/or the like. The pressure sensor may be configured to measure pressure changes (e.g., such as a pressure drop) through the inhaler. The acoustic sensor may be configured to measure air flowing past the acoustic sensor. The sensor may be configured to measure a frequency of a collision of a capsule with a capsule holder of the inhaler. The optical sensor may be configured to measure the passage of powder particles past the sensor.

The inhaler may include multiple dose counters, such as a mechanical dose counter and an electrical dose counter, two different electrical dose counters, etc. The mechanical dose counter and the electrical dose counter (e.g., and possibly multiple different electrical dose counters) may be triggered to increment or decrement a counted dose based on different actuations or actions occurring at the inhaler. For example, the mechanical dose counter may be configured to decrement when the mouthpiece cover is moved from an open position to a closed position to cover the mouthpiece to the user, and the electronic dose counter may be configured to record a dosing event when the mouthpiece cover is moved from the closed position to the open position to expose the mouthpiece and/or record a dosing event when a measurement from the pressure sensor exceeds a threshold (e.g., when a flow rate exceeds a threshold or falls within a particular range).

The inhaler may include a communication circuit that is configured to send a signal indicating the dosing event to an external device. The inhaler may determine that a discrepancy between the mechanical dose counter and the electronic dose counter exceeds a threshold, and may be configured to notify the user of the discrepancy. For example, the inhaler may notify the user of the discrepancy by providing a notification to the user by way of a mobile application residing on the external device, by illuminating one or more light emitting diodes (LEDs) of the inhaler, by outputting an audible signal through a speaker of the inhaler or external device, by sending a text, email, or instant message to the external device or DHP, and/or by providing a notification to the DHP.

The discrepancy between the mechanical dose counter and the electronic dose counter is indicative of a defect of the inhaler and/or misuse or mis-operation of the inhaler by the user. For example, a defect of the inhaler may cause the mechanical dose counter and/or the electrical dose counter to operate incorrectly. Such defect may also cause the dose delivery mechanical of the inhaler to malfunction, which may prevent the user from receiving proper doses of medication. Further, the discrepancy between the dose counters can be indicative of misuse or mis-operation of the inhaler by the user, which may be prevented and corrected earlier if the discrepancy is detected. The inhaler and/or the external device may be configured to provide a notification (e.g., feedback, such as an alert) when the discrepancy between two or more dose readings (e.g., a mechanical dose reading and an electrical dose reading) exceeds a threshold, where the notification alerts the user or HCP to a defect of the inhaler and/or misuse or mis-operation of the inhaler by the user.

An inhaler may include a main body comprising a mouthpiece and medicament. The inhaler may also include an electronics module that includes a processor, memory, a temperature sensor configured to measure temperature of a vicinity in or around the inhaler, and a humidity sensor configured to measure humidity of a vicinity in or around the inhaler. The electronics module may determine that a temperature measurement falls outside of a temperature range and/or that a humidity measurement falls outside of a humidity range. The electronics module may notify a user that the temperature measurement falls outside of the temperature range and/or that the humidity measurement falls outside of the humidity range to notify the user. For example, the electronics module may send a signal to an external device that indicates that the temperature measurement falls outside of the temperature range or that the humidity measurement falls outside of the humidity range to notify the user.

In some examples, the electronics module may also include an orientation sensor configured to make orientation measurements. In such examples, the electronics module may determine that the inhalation device is in an improper position during an actuation of the inhaler that causes a dose of medicament to be prepared for delivery to the user or during delivery of a dose of medicament to the user, and may notify the user that the inhalation device was in the improper position.

In some example, the electronics module may also include a pressure sensor configured to measure pressure changes within the inhaler. In such examples, the electronics module may determine that a pressure measurement exceeds a threshold indicative of delivery of a dose of medicament to a user, and record an inhalation event based on the pressure measurement. The electronics module may associate a temperature measurement and a humidity measurement with the inhalation event. The inhaler may determine an efficacy of the delivery of the dose of medicament using the associated temperature and humidity measurements. Alternatively or additionally, the electronics module may send the inhalation event and associated temperature and humidity measurements to an external device, and the external device may determine an efficacy of the delivery of the dose of medicament using the associated temperature and humidity measurements.

The electronics module may include a second pressure sensor configured to measure pressure changes at a second location within the inhaler. In such instance, the electronics module may determine that pressure measurements from each of the two pressure sensors exceeds a threshold, and record a partial blockage event based on the determination.

The inhaler may detect when the inhaler is removed from a pouch. For example, the electronic module may receive humidity measurements from the humidity sensor periodically, determine that a change in humidity between subsequent humidity measurements exceeds a threshold, and record an "out-of-pouch" event based on the change in humidity.

A system may include an inhaler and a smart pouch. The inhaler may include a mouthpiece and medicament. The smart pouch may include a communication circuit, a humidity sensor configured to measure humidity of a vicinity in or around the smart pouch, and a processor. The smart pouch may be configured to determine when the inhaler is removed from the pouch and record the removal of the inhaler from the pouch in memory. For example, the processor of the smart pouch may determine that a change in humidity between subsequent humidity measurements exceeds a threshold, record an "out-of-pouch" event based on the change in humidity, and send the "out-of-pouch" event to one or more of the inhaler or an external device.

DETAILED DESCRIPTION

Figure 1:
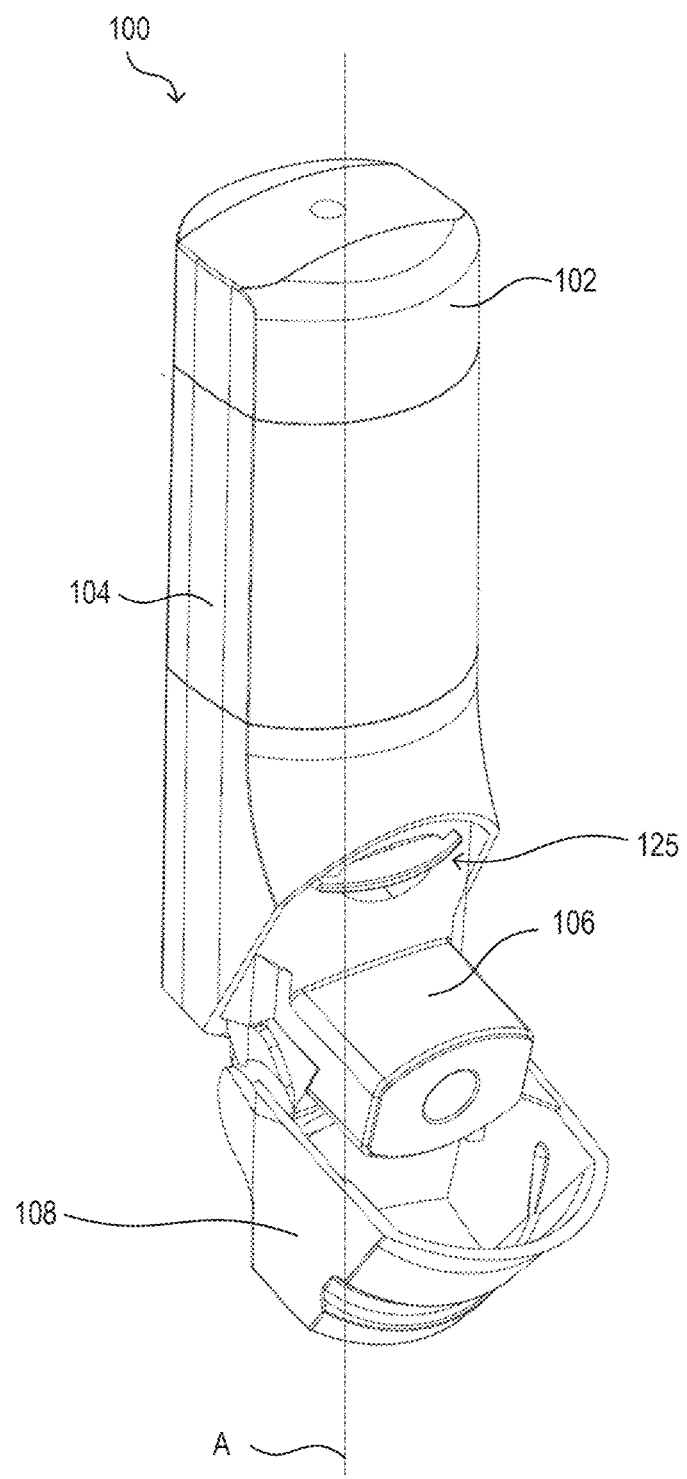
FIG. 1 is a front perspective view of an example inhalation device.

The present disclosure describes devices, systems and methods for sensing, tracking and/or processing usage conditions and parameters associated with a drug delivery device. The devices, systems and methods are described in the context of a breath-actuated inhalation device for delivering medication into a user's lungs. However, the described solutions are equally applicable to other drug delivery devices, such as an injector, a metered-dose inhaler, a nebulizer, a transdermal patch, or an implantable.

Asthma and COPD are chronic inflammatory disease of the airways. They are both characterized by variable and recurring symptoms of airflow obstruction and bronchospasm. The symptoms include episodes of wheezing, coughing, chest tightness and shortness of breath. The symptoms are managed by avoiding triggers and by the use of medicaments, particularly inhaled medicaments. The medicaments include inhaled corticosteroids (ICSs) and bronchodilators.

Inhaled corticosteroids (ICSs) are steroid hormones used in the long-term control of respiratory disorders. They function by reducing the airway inflammation. Examples include budesonide, beclomethasone (dipropionate/dipropionate HFA), fluticasone (propionate), mometasone (furoate), ciclesonide and dexamethasone (sodium). Parentheses indicate examples (e.g., preferred) salt or ester forms.

Different classes of bronchodilators target different receptors in the airways. Two commonly used classes are β2-agonists and anticholinergics. β2-Adrenergic agonists (or "β2-agonists") act upon the β2-adrenoceptors which induces smooth muscle relaxation, resulting in dilation of the bronchial passages. They tend to be categorised by duration of action. Examples of long-acting β2-agonists (LABAs) include formoterol (fumarate), salmeterol (xinafoate), indacaterol (maleate), bambuterol (hydrochloride), clenbuterol (hydrochloride), olodaterol (hydrochloride), carmoterol (hydrochloride), tulobuterol (hydrochloride) and vilanterol (triphenylacetate). Examples of short-acting β2-agonists (SABA) are albuterol (sulfate) and terbutaline (sulfate).

Typically short-acting bronchodilators provide a rapid relief from acute bronchoconstriction (and are often called "rescue" or "reliever" medicines), whereas long-acting bronchodilators help control and prevent longer-term symptoms. However, some rapid-onset long-acting bronchodilators may be used as rescue medicines, such as formoterol (fumarate). Thus, a rescue medicine provides relief from acute bronchoconstriction. The rescue medicine is taken as-needed/prn (pro re nata). The rescue medicine may also be in the form of a combination product, e.g. ICS-formoterol (fumarate), typically budesonide-formoterol (fumarate) or beclomethasone (dipropionate)-formoterol (fumarate). Thus, the rescue medicine is preferably a SABA or a rapid-acting LABA, more preferably albuterol (sulfate) or formoterol (fumarate), and most preferably albuterol (sulfate).

Anticholinergics (or "antimuscarinics") block the neurotransmitter acetylcholine by selectively blocking its receptor in nerve cells. On topical application, anticholinergics act predominantly on the M3 muscarinic receptors located in the airways to produce smooth muscle relaxation, thus producing a bronchodilatory effect. Examples of long-acting muscarinic antagonists (LAMAs) include tiotropium (bromide), oxitropium (bromide), aclidinium (bromide), umeclidinium (bromide), ipratropium (bromide) glycopyrronium (bromide), oxybutynin (hydrochloride or hydrobromide), tolterodine (tartrate), trospium (chloride), solifenacin (succinate), fesoterodine (fumarate) and darifenacin (hydrobromide).

A number of approaches have been taken in preparing and formulating these medicaments for delivery by inhalation, such as via a dry powder inhaler (DPI), a pressurized metered dose inhaler (pMDI) or a nebulizer.

According to the GINA (Global Initiative for Asthma) Guidelines, a step-wise approach can be taken to the treatment of asthma. At step 1, which represents a mild form of asthma, the patient is given an as needed SABA, such as albuterol sulfate. The patient may also be given an as-needed low-dose ICS-formoterol, or a low-dose ICS whenever the SABA is taken. At step 2, a regular low-dose ICS is given alongside the SABA, or an as-needed low-dose ICS-formoterol. At step 3, a LABA is added. At step 4, the doses are increased and at step 5, further add-on treatments are included such as an anticholinergic or a low-dose oral corticosteroid. Thus, the respective steps may be regarded as treatment regimens, which regimens are each configured according to the degree of acute severity of the respiratory disease.

COPD is a leading cause of death worldwide. It is a heterogeneous long-term disease comprising chronic bronchitis, emphysema and also involving the small airways. The pathological changes occurring in patients with COPD are predominantly localized to the airways, lung parenchyma and pulmonary vasculature. Phenotypically, these changes reduce the healthy ability of the lungs to absorb and expel gases.

Bronchitis is characterized by long-term inflammation of the bronchi. Common symptoms may include wheezing, shortness of breath, cough and expectoration of sputum, all of which are highly uncomfortable and detrimental to the patient's quality of life. Emphysema is also related to long-term bronchial inflammation, wherein the inflammatory response results in a breakdown of lung tissue and progressive narrowing of the airways. In time, the lung tissue loses its natural elasticity and becomes enlarged. As such, the efficacy with which gases are exchanged is reduced and respired air is often trapped within the lung. This results in localised hypoxia, and reduces the volume of oxygen being delivered into the patient's bloodstream, per inhalation. Patients therefore experience shortness of breath and instances of breathing difficulty.

Patients living with COPD experience a variety, if not all, of these symptoms on a daily basis. Their severity will be determined by a range of factors but most commonly will be correlated to the progression of the disease. These symptoms, independent of their severity, are indicative of stable COPD and this disease state is maintained and managed through the administration of a variety drugs. The treatments are variable, but often include inhaled bronchodilators, anticholinergic agents, long-acting and short-acting β2-agonists and corticosteroids. The medicaments are often administered as a single therapy or as combination treatments.

Patients are categorized by the severity of their COPD using categories defined in the GOLD Guidelines (Global Initiative for Chronic Obstructive Lung Disease, Inc.). The categories are labelled A-D and the recommended first choice of treatment varies by category. Patient group A are recommended a short-acting muscarinic antagonist (SAMA) prm or a short-acting β2-aginist (SABA) μm. Patient group B are recommended a long-acting muscarinic antagonist (LAMA) or a long-acting β2-aginist (LABA). Patient group C are recommended an inhaled corticosteroid (ICS)+a LABA, or a LAMA. Patient group D are recommended an ICS+a LABA and/or a LAMA.

Patients suffering from respiratory diseases like asthma or COPD suffer from periodic exacerbations beyond the baseline day-to-day variations in their condition. An exacerbation is an acute worsening of respiratory symptoms that require additional therapy, i.e. a therapy going beyond their maintenance therapy.

For asthma, the additional therapy for a moderate exacerbation are repeated doses of SABA, oral corticosteroids and/or controlled flow oxygen (the latter of which requires hospitalization). A severe exacerbation adds an anticholinergic (typically ipratropium bromide), nebulized SABA or IV magnesium sulfate.

For COPD, the additional therapy for a moderate exacerbation are repeated doses of SABA, oral corticosteroids and/or antibiotics. A severe exacerbation adds controlled flow oxygen and/or respiratory support (both of which require hospitalization). An exacerbation within the meaning of the present disclosure includes both moderate and severe exacerbations.

FIG. 1 is a front perspective view of an example inhalation device 100. The example, inhalation device 100 may be a breath-actuated inhalation device. The inhalation device 100 may include a top cap 102, a main housing 104, a mouthpiece 106, a mouthpiece cover 108 and an air vent 125. The top cap 102 may be mechanically attached to the main housing 104. The mouthpiece cover 108 may be hinged to the main housing 104 so that it may open and close to expose the mouthpiece 106. Although illustrated as a hinged connection, the mouthpiece cover 108 may be connected to the inhalation device 100 through other types of connections. Further, in some alternate embodiments, the mouthpiece cover 108 may be omitted.

Figure 2:
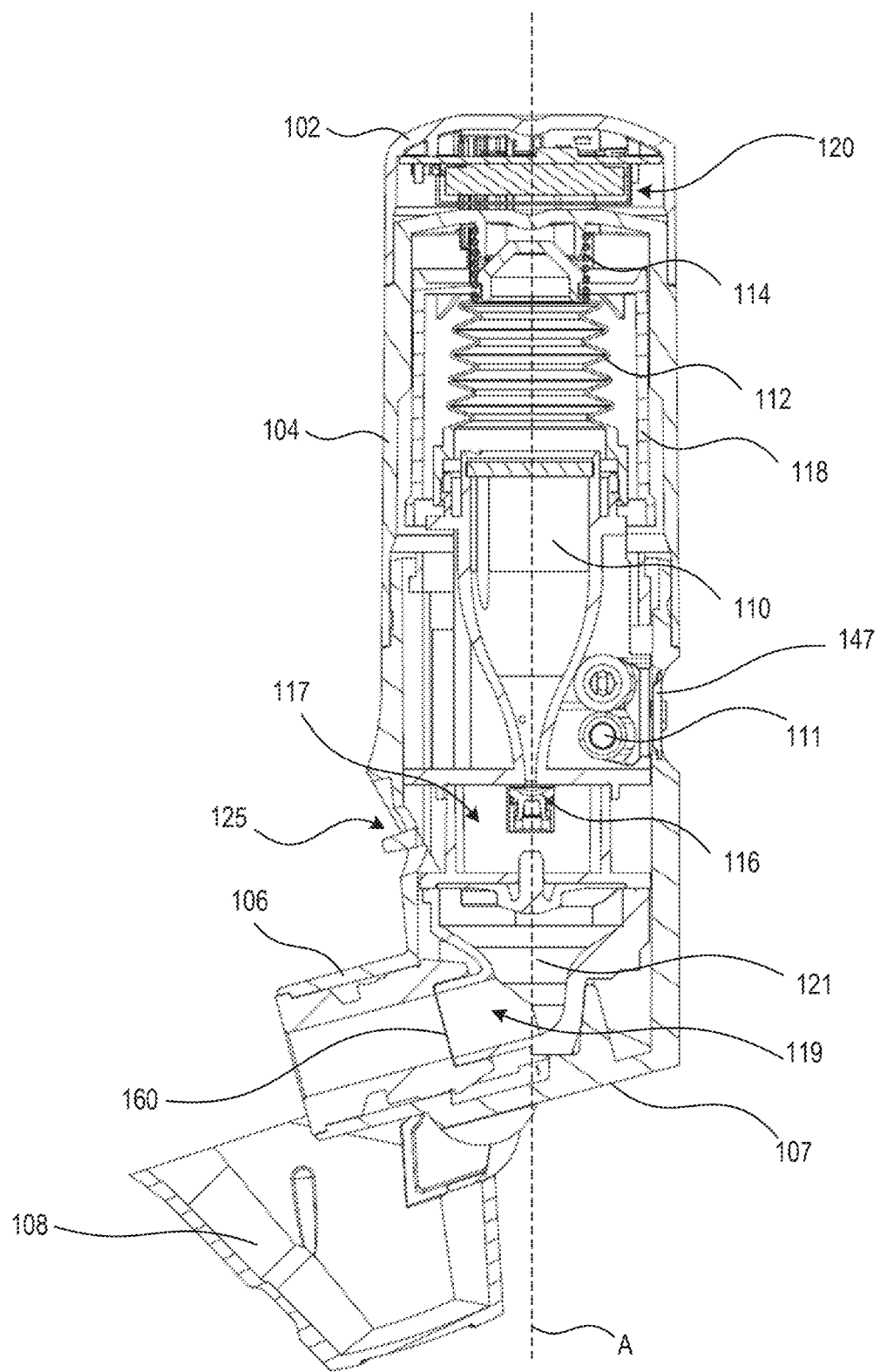
FIG. 2 is a cross-sectional interior perspective view of the example inhalation device.

FIG. 2 is a cross-sectional interior perspective view of the inhalation device 100. Inside the main housing 104, the inhalation device 100 may include a medication reservoir 110 and a dose delivery mechanism. For example, the inhalation device 100 may include a medication reservoir 110 (e.g., a hopper), a bellows 112, a bellows spring 114, a yoke 118, a dose counter 111, a transparent window 147, a dosing cup 116, a dosing chamber 117, a deagglomerator 121 and a flow pathway 119. The medication reservoir 110 may include medication, such as dry powder mediation, for delivery to the user. The yoke 118 may be mechanically coupled (e.g., directly or indirectly) with the mouthpiece cover 108 such that a movement of the mouthpiece cover 108 may result in a movement of the yoke 118. For example, when the mouthpiece cover 108 is moved to expose the mouthpiece 106 (e.g., from a closed position to an open position), the yoke 118 may move vertically (e.g., towards or away from the top cap 102) within the inhalation device 100. Although illustrated as a combination of the bellows 112, the bellows spring 114, the yoke 118, the dosing cup 116, the dosing chamber 117, and the deagglomerator 121, the dose delivery mechanism may include a subset of the components described and/or the inhalation device 100 may include a different dose delivery mechanism (e.g., based on the type of inhalation device, the type of medication, etc.). For instance, in some examples the medication may be included in a blister strip and the dose delivery mechanism (e.g., one or more wheels, levers, and/or actuators) may be configured to advance the blister strip, open a new blister that includes a dose of medication, and make that dose of medication available to a dosing chamber and/or mouthpiece for inhalation by the user.

In the illustrated example dose delivery mechanism of FIG. 1, the movement of the yoke 118 may cause the bellows 112 to compress and deliver a dose of medication from the medication reservoir 110 to the dosing cup 116. Thereafter, a user may inhale through the mouthpiece 106 to receive the dose of medication. The airflow generated from the user's inhalation may cause the deagglomerator 121 to aerosolize the dose of medication by breaking down the agglomerates of the medicament in the dose cup 116. The deagglomerator 121 may be configured to (e.g., fully) aerosolize the medication when the airflow through the flow pathway 119 meets or exceeds a rate or is within a specific range. When aerosolized, the dose of medication may travel from the dosing cup 116, into the dosing chamber 117, through the flow pathway 119, and out of the mouthpiece 106 to the user. If the airflow through the flow pathway 119 does not meet or exceed a rate, or is not within a specific range, some or all of the medication may remain in the dosing cup 116. In the event that the medication in the dosing cup 116 has not been aerosolized by the deagglomerator 121, another dose of medication may not be delivered from the medication reservoir 110 when the mouthpiece cover 108 is subsequently opened. Thus, at least a portion of a dose of medication may remain in the dosing cup until the dose has been aerosolized by the deagglomerator 121.

As the user inhales through the mouthpiece 106, air may enter the air vent 125 to provide a flow of air for delivery of the medication to the user. The flow pathway 119 may extend from the dosing chamber 117 to the end of the mouthpiece 106, and include the dosing chamber 117 and the internal portions of the mouthpiece 106. The dosing cup 116 may reside within or adjacent to the dosing chamber 117.

Figure 3:
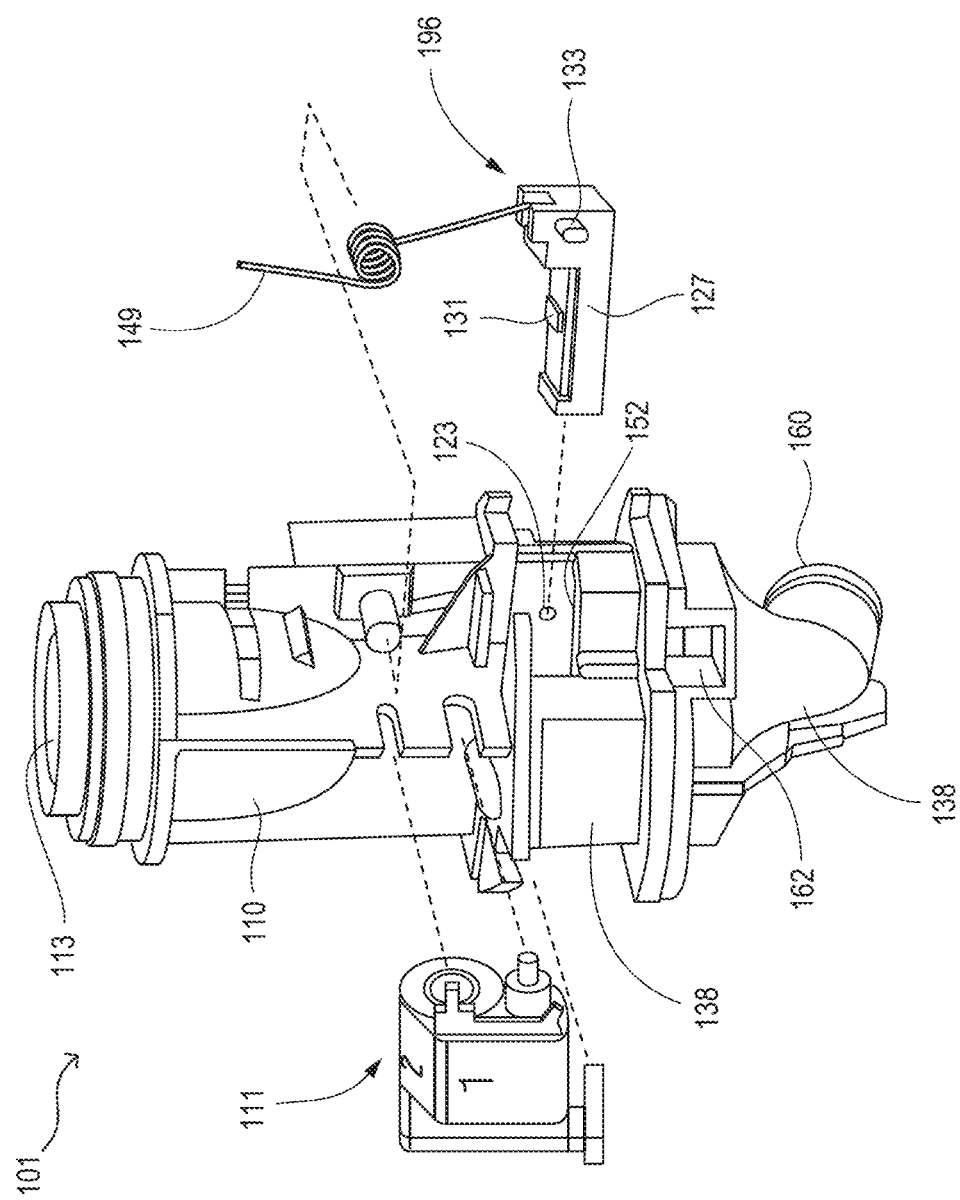
FIG. 3 is an exploded side perspective view of an internal assembly of the inhalation device.

FIG. 3 is an exploded rear perspective view of an internal assembly 101 of the inhalation device 100. The internal assembly 101 may be housed within the main housing 104. The internal assembly 101 may include the medication reservoir 110, which may include an open end 113 and a pressure relief system that includes a relief port 123. A base of the medication reservoir 110 may be secured to a spacer 138, which may be secured to the deagglomerator 121. The deagglomerator 121 may include two diametrically opposed inlet ports 162 that extend substantially tangential to the circular cross-section of the dosing chamber 117. Radial vanes (not shown) may be positioned at the top of the dosing chamber 117 and may be sized such that at least a portion of breath-actuated air streams entering through the diametrically opposed inlet ports 162 collide with the radial vanes. As noted above, when a dose of medication is aerosolized, the dose may travel from the dosing cup 116 into the dosing chamber 117. The dose of medication may then travel to an outlet port 160 of the deagglomerator 121 and pass through the mouthpiece 106 for inhalation by the user.

The internal assembly 101 may include a dose metering system that includes a cup assembly 196. The cup assembly 196 may include a sled 127 with a cup 131 and a boss 133. The sled 127 of the cup assembly 196 may be slidably received in a slide channel 152 of the spacer 138 below the medication reservoir 110. The cup sled 100 may be biased along the slide channel 152 from a dispenser port (not shown) of the medication reservoir 110 towards a delivery passageway by a cup spring 149, which may be secured on the medication reservoir 110. The internal assembly 101 may include the dose counter 111, which may be mechanically coupled (e.g., directly or indirectly) with the mouthpiece cover 108 such that the dose counter 111 may increment or decrement when the mouthpiece is opened or closed. The dose counter 111 may be referred to as a mechanical dose counter, and the reading (e.g., count or number) displayed by the dose counter 111 may be referred to as a mechanical dose reading. The dose counter 111 may initially be set to a number of total doses of medication within the medication reservoir 110. As such, the dose counter 111 may be configured to decrease by one each time the mouthpiece cover 108 is moved from the open position to the closed position (or from the closed position to the open position), thereby indicating the remaining number of doses within the medication reservoir 110. Alternatively, the dose counter 111 may initially be set to zero and may be configured to increase by one each time the mouthpiece cover 108 is moved from the open position to the closed position (or from the closed position to the open position), thereby indicating the total number of doses delivered from the medication reservoir 110.

Although illustrated as being mechanically coupled to the mouthpiece cover 108, in alternate embodiments, such as when the inhalation device 100 includes a different dose delivery mechanism, the dose counter 111 of the inhaler 100 may be coupled (e.g., mechanically coupled) to other components of the inhalation device 100 for incrementing or decrementing. For instance, the dose counter 111 may be coupled (e.g., mechanically coupled) to a switch, lever, or a twist cap that, for example, prepares a dose of medicament for inhalation by the user.

Figure 4A:
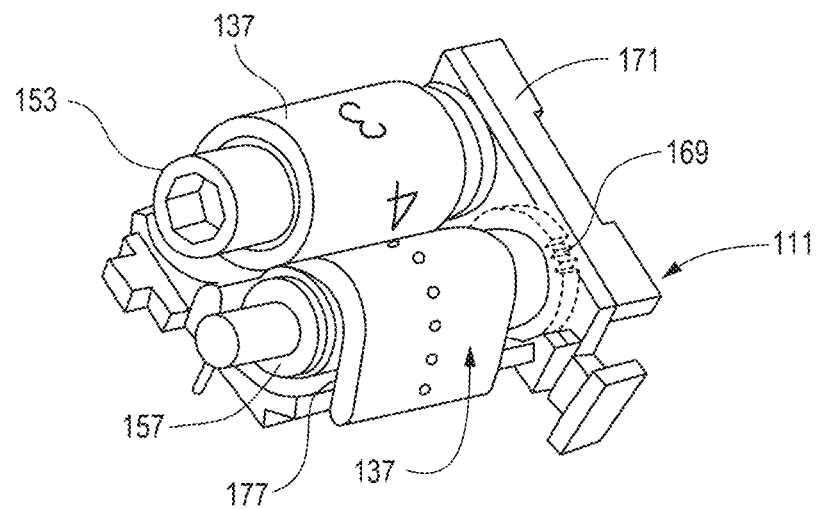
FIGS. 4A and 4B are enlarged perspective views of an example dose counter of the inhalation device.
Figure 4B:
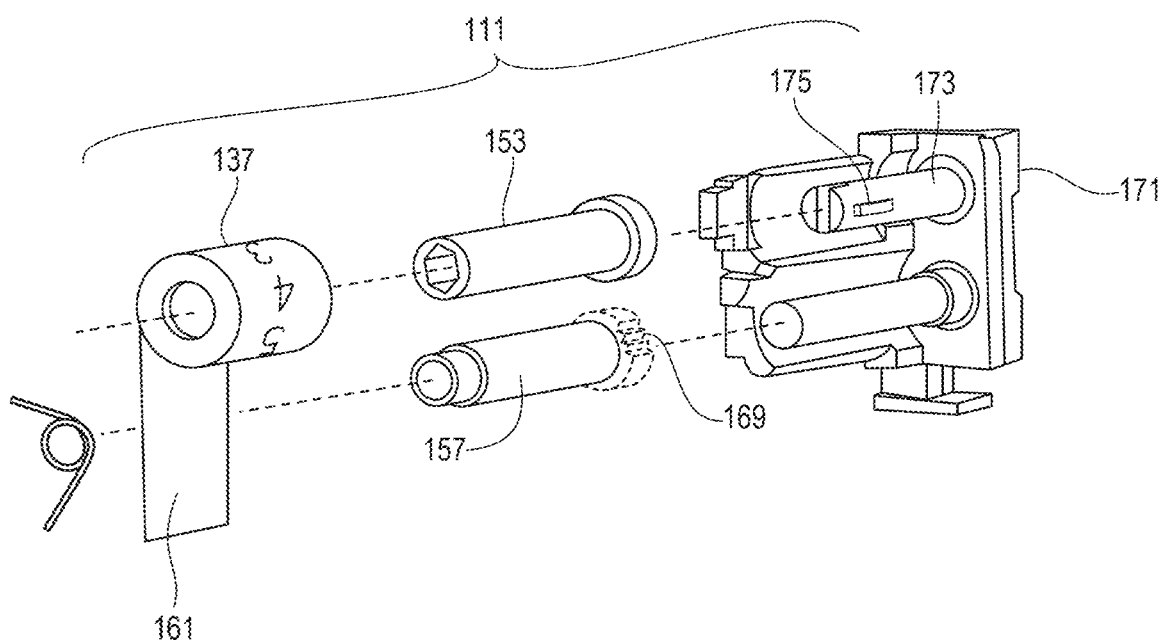

FIGS. 4A and 4B are enlarged perspective views of the dose counter 111 of the inhalation device 100. The dose counter 111 may include a ribbon 137, which may have successive numbers or other suitable indicia printed thereon. The indicia may be in alignment with the transparent window 147 provided in the housing 104 (see FIG. 2). The dose counter 111 may include a rotatable bobbin 153 and a rotatable indexing spool 157. The ribbon 137 may be rolled and received on the bobbin 153. A first end 161 of the bobbin 153 may be secured to the spool 157. When the ribbon 137 unrolls from the bobbin 132, the indicia may be successively displayed as the spool 157 is rotated or advanced.

The spool 157 may be arranged to rotate upon movement of the yoke 118, which may cause a dose of medication to be delivered from the reservoir 110 into the dosing cup 116. As such, the indicia (e.g., a number) on the ribbon 137 may advance to indicate that another dose has been dispensed by the inhalation device 100. The indicia on the ribbon 137 may be arranged such that the indicia (e.g., the numbers) increase or decrease upon rotation of the spool 157. For example, the numbers may decrease upon rotation of the spool 157 to indicate the number of doses remaining in the inhalation device 100 or the numbers may increase upon rotation of the spool 157 to indicate the number of doses dispensed by the inhalation device 100. The spool 157 may include radially extending teeth 169, which may be configured to engage a pawl (not shown) on the yoke 118. The pawl may be configured to engage the teeth 169 and to advance the indexing spool 157 upon the movement of the yoke 118 (e.g., when the mouthpiece cover 108 is being open or closed).

The dose counting 111 may include a chassis 171 that is configured to secure the dose counter 111 to the reservoir 110. The chassis may include one or more includes shafts 173 for receiving the bobbin 153 and the indexing spool 157. The shaft 173 may be forked and may include one or more radial nubs 175, which may be configured to create a resilient resistance to rotation of the bobbin 153 and/or the spool 157 on the shaft 173. A clutch spring 177 may be received on the end of the indexing spool 157 and secured (e.g., locked) to the chassis 171 to allow rotation of the spool 157 in a single direction (e.g., clockwise or counter-clockwise).

Figure 5:
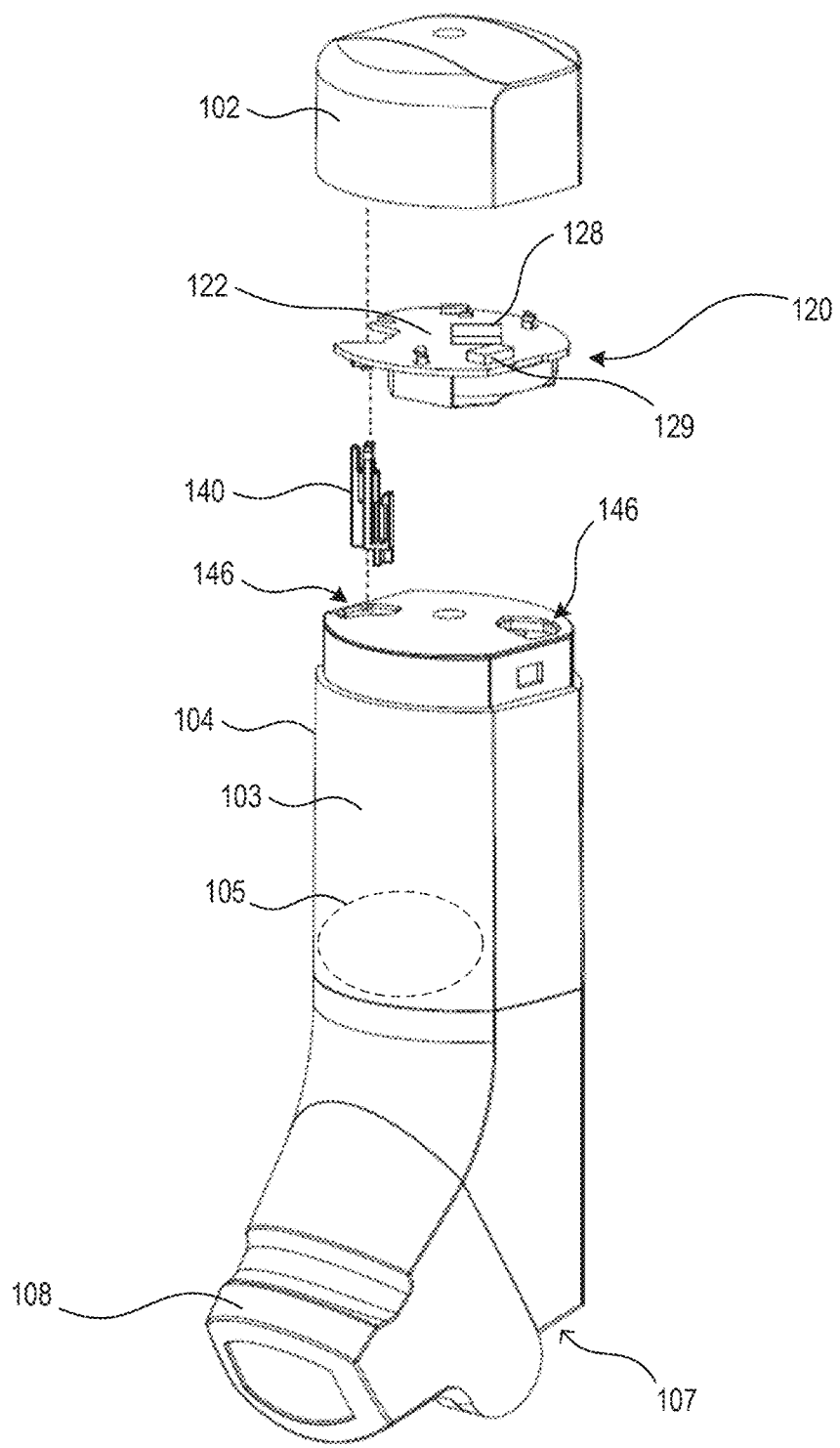
FIG. 5 is an exploded perspective view of the inhalation device with a top cap removed to expose an electronics module.

FIG. 5 is an exploded perspective view of the example inhalation device 100 with the top cap 102 removed to expose an electronics module 120. The top cap 102 may house the electronics module 120, which may include a printed circuit board (PCB) assembly 122. The PCB assembly 122 may include one or more components, such as a sensor system 128 and a wireless communication circuit 129. The top cap 102 may be attached to the main housing 104 via one or more clips (not shown) that engage recesses on the main housing 104. The top cap 102 may overlap a portion of the main housing 104 when connected, for example, such that a substantially pneumatic seal exists between the top cap 102 and the main housing 104. The top surface of the main housing 104 may include one or more (e.g., two) orifices 146. One of the orifices 146 may be configured to accept a slider 140. For example, when the top cap 102 is attached to the main housing 104, the slider 140 may protrude through the top surface of the main housing 104 via one of the orifices 146. The top cap 102 may be removably attached to the main housing 104. Alternatively or additionally, the electronics module 120 may be integrated within the main housing 104 and/or the top cap 102 housing the electronics module 120 may be permanently attached to the main housing 104.

Further, in some examples, the electronics module 120 may reside is a separate device that is outside of and separate from the inhalation device 100. For instance, the electronics module 120 may reside within an add-on device that is configured to attached to and subsequently removed from the inhalation device 100, for example, when the inhalation device 100 runs out of medication or expires. In such instances, the user may attached the add-on device that includes the electronics module 120 from one inhalation device 100 to another each time the user receives a new inhalation device 100. The add-on device may be configured to be attached to any component of the inhalation device 100, such as the main housing 104, the mouthpiece, and/or a medication canister housed within the main housing of the main housing 104 of the inhalation device 100 (e.g., such that the sensors are in fluid communication with the mouthpiece and/or flow channel of inhalation device 100.

Figure 6:
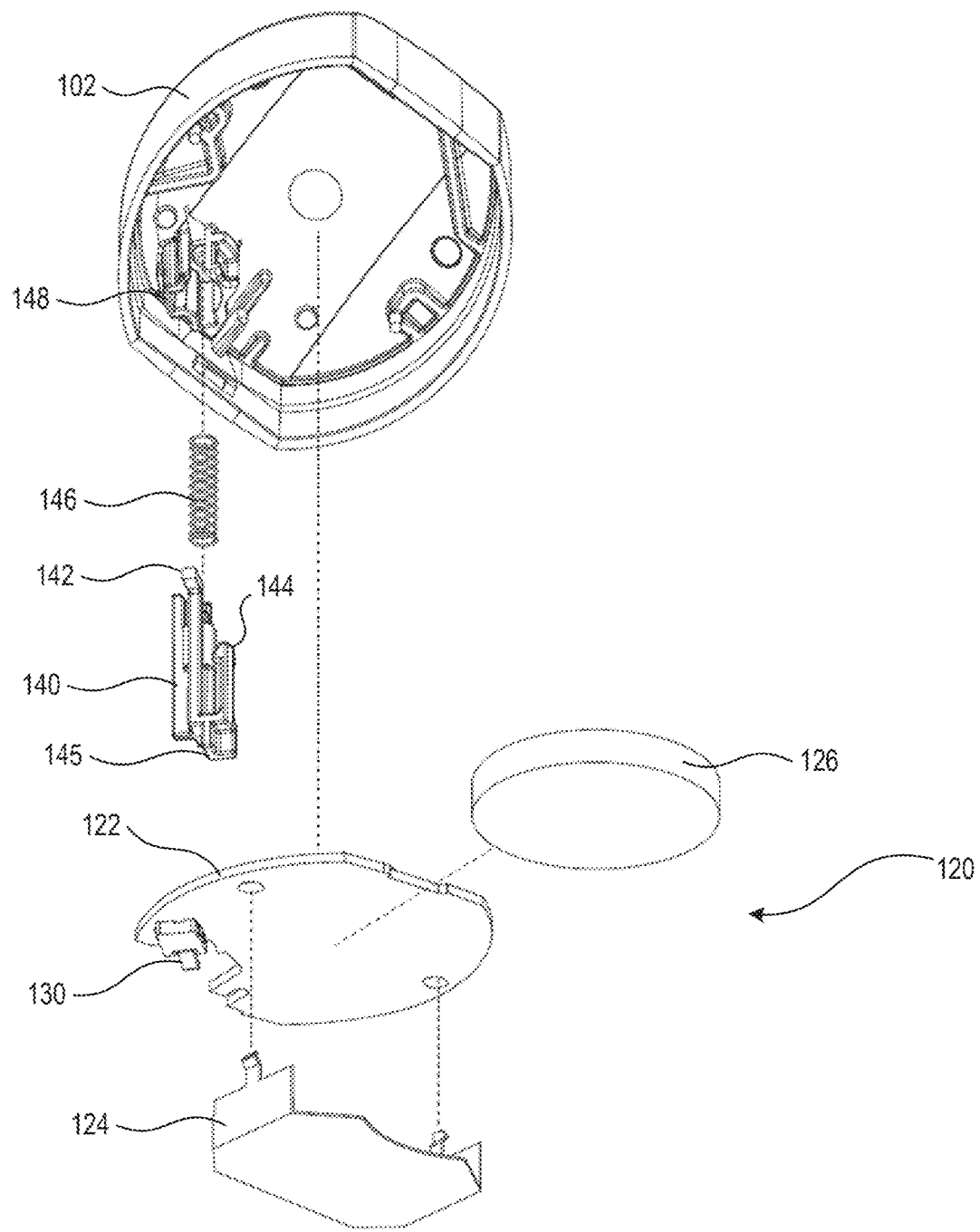
FIG. 6 is an exploded perspective view of the top cap and the electronics module of the inhalation device.

FIG. 6 is an exploded perspective view of the top cap 102 and the electronics module 120. As shown in FIG. 6, the slider 140 may define an arm 142, a stopper 144, and a distal base 145. The distal end 145 may be a bottom portion of the slider 140. The distal end 145 of the slider 140 may be configured to abut the yoke 118 that resides within the main housing 104. The top cap 102 may include a slider guide 148 that is configured to receive a slider spring 146 and the slider 140. The slider spring 146 may reside within the slider guide 148. The slider spring 146 may engage an inner surface of the top cap 102, and the slider spring 146 may engage (e.g., abut) an upper portion (e.g., a proximate end) of the slider 140.

When the slider 140 is installed within the slider guide 148, the slider spring 146 may be partially compressed between the top of the slider 140 and the inner surface of the top cap 102. For example, the slider spring 146 may be configured such that the distal end 145 of the slider 140 remains in contact with the yoke 118 when the mouthpiece cover 108 is closed. The distal end 145 of the slider 145 may also remain in contact with the yoke 118 while the mouthpiece cover 108 is being opened or closed. The stopper 144 of the slider 140 may engage a stopper of the slider guide 148, for example, such that the slider 140 is retained within the slider guide 148 through the opening and closing of the mouthpiece cover 108, and vice versa. The stopper 144 and the slider guide 148 may be configured to limit the vertical (e.g., axial) travel of the slider 140. This limit may be less than the vertical travel of the yoke 118. Thus, as the mouthpiece cover 108 is moved to an open position, the yoke 118 may continue to move in a vertical direction towards the mouthpiece 106 but the stopper 144 may stop the vertical travel of the slider 140 such that the distal end 145 of the slider 140 may no longer be in contact with the yoke 118.

The electronics module 120 may include one or more components, such as the sensor system 128, the wireless communication circuit 129, a switch 130, a power supply (e.g., a battery 126), a battery holder 124, an indicator (e.g., a light emitting diode (LED)), a controller (e.g., processor) and/or memory. When used herein, the terms controller and processor may be used interchangeably. One or more of the components of the electronics module 120 may be mounted on, and electrically coupled to, the PCB 122. The controller and/or memory may be physically distinct components of the PCB 122. Alternatively, the controller and memory may be part of a chipset mounted on the PCB 122. For example, the wireless communication circuit 129 may include the controller and/or memory for the electronics module 120. The controller of the electronics module 120 may include a microcontroller, a programmable logic device (PLD), a microprocessor, an application specific integrated circuit (ASIC), a field-programmable gate array (FPGA), or any suitable processing device or control circuit. The memory may include computer-executable instructions that, when executed by the controller, cause the controller to implement the processes of the electronics module as described herein.

The controller may access information from, and store data in the memory. The memory may include any type of suitable memory, such as non-removable memory and/or removable memory. The non-removable memory may include random-access memory (RAM), read-only memory (ROM), a hard disk, or any other type of memory storage device. The removable memory may include a subscriber identity module (SIM) card, a memory stick, a secure digital (SD) memory card, and the like. The memory may be internal to the controller. The controller may also access data from, and store data in, memory that is not physically located within the electronics module 120, such as on a server or a smartphone.

The battery 126 may provide power to the components of the PCB 122. The battery 126 may be any suitable source for powering the electronics module 120, such as a coin cell battery, for example. The battery 126 may be rechargeable or non-rechargeable. The battery 126 may be housed by the battery holder 124. The battery holder 124 may be secured to the PCB 122 such that the battery 126 maintains continuous contact with the PCB 122 and/or is in electrical connection with the components of the PCB 122. The battery 126 may have a battery capacity that may affect the life of the battery 126. As will be further discussed below, the distribution of power from the battery 126 to the one or more components of the PCB 122 may be managed to ensure the battery 126 can power the electronics module 120 over the useful life of the inhalation device 100 and/or the medication contained therein.

The switch 130 may be actuated by the dose delivery mechanism of the inhalation device 100. When incorporated using the example dose delivery mechanism described herein, the switch 130 may be actuated by a slider 140 as the mouthpiece cover 108 is moved from a closed position to an open position. Although it should be appreciated that if the inhalation device 100 includes a different dose delivery mechanism, then the switch 130 may be actuated by a different component of the dose deliver mechanism. When the switch 130 is actuated, the electronics module 120 may generate a signal causing the electronics module 120 to change states, such as from an off or sleep state to an active state. When in the active state, the controller of the electronics module 120 may wake and provide power to the sensor system 128 to enable the sensor system 128 to take measurement readings. Further, the electronics module 120 may store a dosing event (e.g., which may be referred to as a dose delivery event or an actuation event) each time the switch 130 is actuated. As described in more detail below, the electronics module 120 may have a plurality of power states, each with respective power consumption levels. For example, the electronics module 120 may be configured to operate in a system off state, a sleep state, and/or an active state, where the electronics module 120 consumes the least amount of power while in the off state (e.g., no power or just enough to run a clock), the sleep state uses more power than the off state (e.g., to drive the memory, the communication circuit, and/or a timer or clock), and the active state uses the most amount of power (e.g., to drive the controller, one or more sensors, the communication circuit, potentially in a faster advertising mode than the sleep state, and/or a timer or clock).

The sensor system 128 may include one or more sensors, such as one or more pressure sensors, temperature sensors, humidity sensors, acoustic sensors, optical sensors, orientation sensors, and/or the like. The pressure sensor(s) may include a barometric pressure sensor (e.g., an atmospheric pressure sensor), a differential pressure sensor, an absolute pressure sensor, and/or the like. The sensors may employ microelectromechanical systems (MEMS) and/or nanoelectromechanical systems (NEMS) technology. The pressure sensor(s) may be configured to provide an instantaneous pressure reading to the controller of the electronics module 120 and/or aggregated pressure readings over time. As illustrated in FIGS. 2 and 5, the pressure sensor(s) may reside within the inhalation device 100 but remain outside of the flow pathway 119. Accordingly, the pressure sensor(s) may be configured to measure a plurality of atmospheric pressures within the inhalation device 100.

The electronics module 120 (e.g., and/or a mobile application residing on an external device) may use measurements from the sensor system 128 to determine one or more dosing events. For example, the electronics module 120 may be configured to compare one or more measurements from the sensor system 128 to one or more threshold values to categorize an inhalation event as a no/low inhalation event, a fair inhalation event, a good inhalation event, an excessive inhalation event, and/or an exhalation event. For example, the electronics module may generate a good inhalation event when the measurements from the sensor system 128 indicate a flow rate in a particular range (e.g., between 200 liters per min (L/min) and 45 L/min), generate a fair inhalation event when the measurements from the sensor system 128 indicate a flow rate in another range (e.g., 30 L/min and 45 L/min), generate a no inhalation event when the measurements from the sensor system 128 indicate a flow rate that is less than a threshold value (e.g., 30 L/min), and an excessive inhalation event when the measurements from the sensor system 128 indicate a flow rate that is greater than an upper threshold (e.g., greater than 200 L/min).

The temperature sensor(s) may include a thermistor, a thermocouple, a resistance temperature detector, a temperature sensor chip and the like. The temperature sensor(s) may be configured to provide a temperature reading to the controller of the electronics module 120 and/or aggregated temperature readings over time. The temperature sensor(s) may be configured to measure the external temperature in the space proximate to the inhalation device 100. Accordingly, main housing 104 and/or the top cap 102 may include an opening (e.g., a vent) to allow for the temperature sensor(s) to measure the ambient temperature external to the housing.

Alternatively or additionally, the temperature sensor(s) may be configured to measure temperature within the inhalation device 100, such as within one or more of the top cap 102, the main housing 104, and/or the mouthpiece 106 of the inhalation device 100. The ability to measure both internal and external temperature may allow the electronics module 120 to determine the operating temperature of the components of the electronics module 120, the temperature of the air flowing through the inhalation device 100 when a user inhales through the inhalation device 100, etc. Accordingly, the electronics module 120 may be configured to detect an over or under temperature condition, such as an over temperature condition of one or more of the components of the electronic module 120 (e.g., such as another sensor, like a pressure sensor), an over temperature condition of the inhalation device 100, an ambient temperature that exceeds a threshold, etc. The electronics module 120 may be configured to cause the communication circuit 129 to transmit a temperature message to an external device (e.g., a mobile device) that indicates an over temperature condition, an ambient temperature reading, and/or a temperature reading of internal to the inhalation device 100 (e.g., such as a temperature change detected through the flow channel of the inhalation device 100).

The temperature sensor(s) may be located on the electronics module 120. For example, in some embodiments, the temperature sensor(s) may be embedded within the pressure sensor (e.g., embedded within a barometric pressure sensor). The temperature of the other components of the electronics module 120 and/or the temperature of the user's hand may affect the measurements of the temperature sensor. Accordingly, in some embodiments, at least a portion of the temperature sensor(s) may be located external to the electronics module 120, such as within the main housing 104. In such examples, the temperature sensor(s) may include an electronic connection to the controller of the electronics module 120. Further, to avoid being affected by the temperature of the user's hand, the temperature sensor(s) may be located on the front 103 of the main housing 104 or on the bottom 107 of the main housing 104. For example, the temperature sensor(s) may be located on the front side 103 of the main housing 104 within a region 105 (e.g., as illustrated in FIG. 5) that is proximate to (e.g., above) the air vent 125. The temperature sensor(s) may also be located on the bottom 107 of the main housing 104, so that, for example, the mouthpiece cover 108 may inhibit the user from placing their fingers near the temperature sensor(s) when the mouthpiece cover 108 is in the open position.

The temperature sensor(s) may be configured to take temperature measurements when the electronics module 120 is in an active state (e.g., when in the measurement mode of the active state, as described herein). For example, the temperature sensor(s) may be configured to take temperature measurements at the same time the pressure sensor is taking pressure measurements, which for example, may be for a predetermined amount of time (e.g., 1-3 minutes) after the mouthpiece cover 108 is moved into the open position. Alternatively or additionally, the temperature sensor(s) may periodically take pressure measurements while the mouthpiece cover 108 is in a closed state (e.g., when the electronics module 120 periodically wakes from a sleep state to enter an advertising state).

The humidity sensor(s) may include a capacitive sensor, a resistive sensor, a thermal conductivity sensor, and/or the like. The humidity sensor(s) may be configured to provide a humidity reading to the controller of the electronics module 120 and/or aggregated humidity readings over time. The humidity sensor(s) may be configured to measure environmental conditions (e.g., external humidity levels in an area around the inhalation device 100) and/or the humidity level within a particular location within the inhalation device 100. The humidity sensor(s) may be configured to measure relative humidity.

The humidity sensor(s) may be located on the electronics module 120. For example, the humidity sensor(s) may be incorporated into the electronics module 120. The humidity sensor(s) may be affected by the moisture of user's hand. Accordingly, in some embodiments, at least a portion of the humidity sensor(s) may be located external to the electronics module 120, such as within the main housing 104. In such examples, the humidity sensor(s) may include an electronic connection to the controller of the electronics module 120. Further, to avoid being affected by moisture caused by the user's hand, the humidity sensor(s) may be located on the front 103 of the main housing 104 or on the bottom 107 of the main housing 104. For example, the humidity sensor(s) may be located on the front side 103 of the main housing 104 within a region 105 (e.g., as illustrated in FIG. 5) that is proximate to (e.g., above) the air vent 125. The humidity sensor(s) may also be located on the bottom 107 of the main housing 104, so that, for example, the mouthpiece cover 108 may inhibit the user from placing their fingers near the humidity sensor(s) when the mouthpiece cover 108 is in the open position.

The humidity sensor(s) may be configured to measure humidity, such as the ambient humidity external to the inhalation device 100. Accordingly, main housing 104 and/or the top cap 102 may include an opening (e.g., a vent) to allow for the humidity sensor(s) to measure the ambient humidity external to the housing. Alternatively or additionally, the humidity sensor(s) may be configured to measure humidity within the inhalation device 100, such as within one or more of the top cap 102, the main housing 104, and/or the mouthpiece 106 of the inhalation device 100. The ability to measure both internal and humidity may allow the electronics module 120 to determine the whether there is a risk that the dry powdered medicament could clump together. Accordingly, the electronics module 120 may be configured to detect an over or under humidity condition, and may be configured to cause the communication circuit 129 to transmit a humidity message to an external device (e.g., a mobile device).

The humidity sensor(s) may be configured to take humidity measurements when the electronics module 120 is in an active state (e.g., when in the measurement mode of the active state, as described herein). For example, the humidity sensor(s) may be configured to take humidity measurements at the same time the pressure sensor is taking pressure measurements, which for example, may be for a predetermined amount of time (e.g., 1-3 minutes) after the mouthpiece cover 108 is moved into the open position. Alternatively or additionally, the humidity sensor(s) may periodically take pressure measurements while the mouthpiece cover 108 is in a closed state (e.g., when the electronics module 120 periodically wakes from a sleep state to enter an advertising state).

The orientation sensor(s) may include an accelerometer, a gravity (G) sensor, a gyroscope, a magnetometer and the like. The orientation sensor(s) may be configured to provide an orientation reading (e.g., acceleration, rotation, direction, etc.) to the controller of the electronics module 120 and/or aggregated orientation readings over time. The orientation sensor(s) may be located on the electronics module 120. For example, the orientation sensor(s) may be incorporated into the electronics module 120.

The orientation sensor(s) may be configured to take orientation measurements when the electronics module 120 is in an active state (e.g., when in the measurement mode of the active state, as described herein). For example, the orientation sensor(s) may be configured to take orientation measurements at the same time the pressure sensor is taking pressure measurements, which for example, may be for a predetermined amount of time (e.g., 1-3 minutes) after the mouthpiece cover 108 is moved into the open position. Accordingly, the electronics module 120 may be configured to use feedback from the orientation sensor(s) to determine whether the inhalation device 100 was in the proper orientation when a dose of medication is metered from the medication reservoir 110 to the dosing cup 116 and/or during the inhalation of the dose of medication by a user.

For instance, the electronics module 120 may use feedback from the orientation sensor to determine whether the inhalation device 100 is used in an improper position, such as upside down (i.e., with the cap 102 oriented below the mouthpiece 106). Improper orientation of the inhalation device 100 (e.g., or any pMDI) can be indicative of a misuse of the inhalation device 100, for example, because medicament may not be properly administered when the inhalation device 100 is in an improper position. Further, some users use the inhalation device 100 when lying down. Accordingly, feedback from the orientation sensor allows the electronics module 120 to determine and notify to a user that use of the inhaler (e.g., delivery of the medication, preparation of the mediation, such as a valve refilling, and/or the like) was negatively affected, and as such, the dose of medicine may not be properly delivered.

Figure 8:
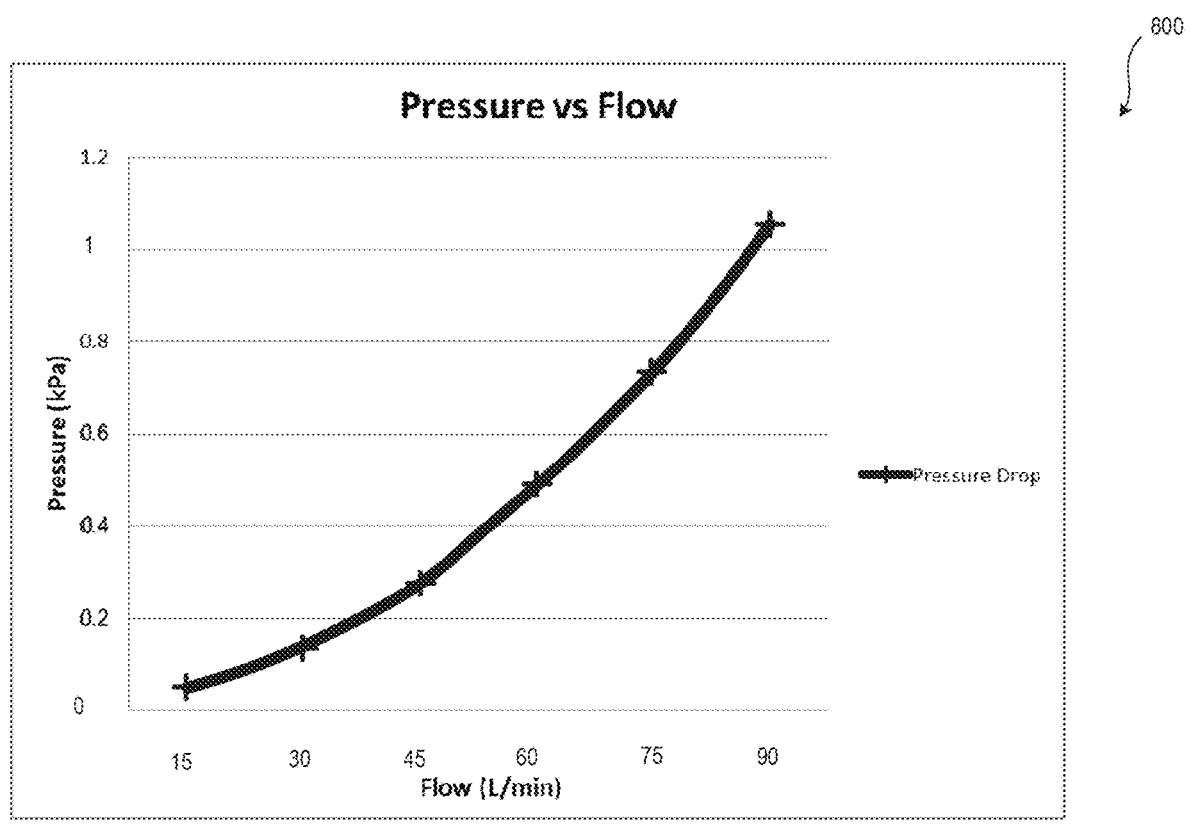
FIG. 8 is a graph of an exemplary relationship between pressure measurements and airflow rates through a flow pathway of the inhalation device.

The controller of the electronics module 120 may receive signals corresponding to the readings from the sensor system 128. The controller may compute, estimate, or otherwise determine one or more parameters (e.g., a peak flow rate, a time to peak flow rate, an inhaled volume, an inhalation duration, a temperature, a humidity level, an orientation of the inhalation device 100, etc.) using the signals received from the sensor system 128. The flow rate parameters, for example, may be indicative of a profile of airflow through the flow pathway 119 of the inhalation device 100. For example, if the pressure sensor(s) records a change in pressure of 0.3 kilopascals (kPA), the electronics module 120 may determine that the change corresponds to an airflow rate of approximately 45 liters per minute (Lpm) through the flow pathway 119. FIG. 8 depicts a graph 800 showing an example relationship between pressure measurements obtained by the sensor system 128 and airflow rates through the flow pathway 119. It will be appreciated that the profile shown in FIG. 8 is merely exemplary and that the determined airflow rates may depend on the size, shape, and/or design of the inhalation device 100 and its internal components.

As described in more detail with reference to FIG. 9, the inhalation device 100 may include a communication circuit, such as a Bluetooth radio, for transferring data to an external device (e.g., a mobile device 902, a wearable, etc.). The external device may include software (e.g., a mobile application) or a web interface to allow for display of data to the user. The inhalation device 100 may transfer data received from one or more of the sensors of the inhalation device 100 to the external device. For example, the temperature and humidity data determined by the temperature and humidity sensors may be indicative of the microenvironment in which the inhalation device 100 was used (e.g., as opposed to more general weather data based on the location of the external device). The conditions in which the inhalation device 100 is used (e.g., which may be indoors) may be different from general location-based weather information.

As noted above, the sensors (e.g., the temperature, humidity, and/or orientation sensors) may detect the measurements at the time of the inhaler's use or may take periodic measurements. Further, the electronics module 120 may determine a baseline humidity measurement on the date at which the inhalation device 100 is taken out of a protective pouch. The pouch may be the packaging that the inhalation device 100 is delivered to the user to prior to first use of the inhalation device 100 by the user. For example, the inhalation device 100 may be in a controlled low humidity environment when it is taken out of the pouch. Thereafter, the inhalation device 100 may determine a spike in humidity if humidity measurements are taken periodically.

The inhalation device 100 may detect when it is removed from the pouch, for example, based on measurements received from the sensor system 128. The inhalation device 100 may generate an out-of-pouch event upon detecting that it has been removed from the pouch. The out-of-pouch event may indicate one or more characteristics of the inhalation device 100 when it was removed from the pouch, such as, but not limited to the time it was removed from the pouch, the relative temperature or humidity of the inhalation device 100 and/or the environment when the inhalation device was removed from the pouch, etc.

The inhalation device 100 may also detect whether it has been removed from the pouch and/or the amount of delay between the inhalation device 100 being taken out of the pouch and the first use of the inhalation device 100, for example, based on measurements received from the sensor system 128 (e.g., such as humidity changes over a particular threshold). Further, the inhalation device 100 may determine the time "out-of-pouch", which may be the total time period since the inhalation device 100 had been removed from the pouch (e.g., and may be indicative of the inhaler's life span). The inhalation device 100 may record when the inhalation device 100 is removed from the pouch, record the total amount of time that the inhalation device 100 is out of the pouch, and provide a notification (e.g., possibly via the mobile application) to the user when the time out of pouch has exceed a threshold time period (e.g., rather than based on a total number of dosing events or a time period from the first usage of the inhalation device 100).

In some examples, the pouch may be a smart pouch. For example, a smart pouch may correspond to a pouch that includes electronics (e.g., such as all or a subset of the components of the electronics module 120). For example, the electronics of a smart pouch may be configured to determine the humidity and/or temperature of the environment of the inhalation device 100 when the inhalation device 100 is removed from of the pouch. The smart pouch may then communicate the temperature and/or humidity measurement, potentially along with a timestamp of when the inhalation device 100 was removed from the pouch, to the external device and/or the inhalation device 100. In some examples, the pouch and/or the inhalation device 100 may include near field communication (NFC) chipsets, and the pouch and/or inhalation device 100 could detect when the inhalation device 100 moves away from the pouch using the NFC communication protocol.

The inhalation device 100 may receive temperature and/or humidity measurements periodically and/or at the time of a use of the inhaler (e.g., as determine by an opening of the mouthpiece cover 108 and/or by a pressure measurement that exceeds a threshold indicative of inhalation). The inhalation device 100 and/or the external device may monitor and determine the conditions in which the inhalation device 100 is stored using periodic temperature and/or humidity measurements. The inhalation device 100 and/or the external device may alert the user if the temperature and/or humidity measurements exceed the limits defined by the instructions for use (IFU) (e.g., if the measurements exceed the limits once, exceed the limits a number of times over a predefined time period, and/or the like). The inhalation device 100 and/or the external device may determine the temperature and/or humidity of the inhalation device 100 (e.g., and/or the environment surrounding the inhalation device 100) at the times which the inhalation device 100 is used. For example, if the inhalation device 100 is used or stored in a hot and/or humid environment, such as in a bathroom or shower, the dry powder medicament of the inhalation device 100 may be adversely affected.

The inhalation device 100 (e.g., and/or an external device) may be configured to determine or predict that the inhalation device 100 may fail based on the temperature and/or humidity measurements. For example, if the temperature and/or humidity measurements indicate that the inhalation device 100 is used in an environment that has a temperature or humidity above a predetermined threshold or above the threshold for a predetermined number of times of use (e.g., above the threshold more than 10 times), the inhalation device 100 may determine that the inhalation device 100 is of greatly likelihood to fail or mis-operate, and the inhalation device 100 may alert the user accordingly (e.g., through the use of an onboard LED, through the external device, etc.).

In some example, the inhalation device 100 may include a plurality of pressure sensors. In such instances, the pressure sensors may be located at different places within the inhalation device 100. Accordingly, the inhalation device 100 may be configured to detect a partial blockage of the inhalation device 100 based on a difference between the pressure measurements of the multiple pressure sensors exceeding a predetermined threshold. For example, the inhalation device 100 may be configured to determine that medicament (e.g., dry powder medicament) is blocking the air vent 125 based on the difference between the pressure measurements of the multiple pressure sensors exceeding a predetermined threshold. The inhalation device 100 may provide a notification to the user, a manufacturer of the inhaler, or a health care provider (HCP) based on the difference between the pressure measurements of the multiple pressure sensors exceeding the predetermined threshold. The inhalation device 100 may provide the notification directly (e.g., an audio alert and/or illuminating a light source) and/or may send the data and/or the notification to an external device (e.g., smartphone), and the external device may provide the notification to the user.

The humidity and/or temperature at the time of use of the inhalation device 100 may affect delivery of the medicine to the lungs of the user. For example, a user's lungs/airways may be more opened up in higher humidity and may be more constricted in colder temperatures. Accordingly, the drug delivery of the inhalation device 100 may be affected by relaxed or constricted airways, which for example, may lead to either controlled or uncontrolled asthma in the user.

The controller of the electronics module 120 may compare signals received from the sensor system 128 and/or the determined parameters to one or more thresholds or ranges, for example, as part of an assessment of how the inhalation device 100 is being used, the conditions under which the inhalation device 100 is being used or stored, and/or whether the use or storage may affect the delivery of a dose of medication. For example, where the determined airflow metric corresponds to an inhalation with an airflow rate below a particular threshold, the electronics module 120 may determine that there has been no inhalation or an insufficient inhalation from the mouthpiece 106 of the inhalation device 100. If the determined airflow metric corresponds to an inhalation with an airflow rate above a particular threshold, the electronics module 120 may determine that there has been an excessive inhalation from the mouthpiece 106. If the determined airflow metric corresponds to an inhalation with an airflow rate within a particular range, the electronics module 120 may determine that the inhalation is "good", or likely to result in a full dose of medication being delivered.

As noted above, the electronics module 120 may include indicators, such as an LED. The indicators may be configured to provide feedback to users regarding their use of the inhalation device 100 and/or the conditions under which the inhalation device 100 is being used or stored. Thus, in one example, the electronics module 120 may cause an LED may illuminate, change color, and/or flash if the orientation of the inhalation device 100 falls outside of an orientation range (e.g., any measured orientation angle greater than forty-five (45) degrees from an optimal orientation angle, for example, as defined by the axis "A" illustrated in FIGS. 1 and 2). Similarly, the electronics module 120 may cause an LED may illuminate, change color, and/or flash if an ambient and/or internal temperature of the inhalation device 100 falls outside of a temperature range (e.g., outside the storage range specified for the inhalation device 100). Further, the electronics module 120 may cause an LED to illuminate, change color, and/or flash if an ambient and/or internal humidity of the inhalation device 100 falls outside of a humidity range. In some examples, the humidity range is a relative humidity range specified in the IFU, which for example, may be associated with a particular time period (e.g., 13 months for a humidity above a particular for an albuterol-containing inhalers, 1 month for a fluticasone-containing inhalers)).

Although described as being performed at the inhalation device 100, the parameters may be computed and/or assessed via one or more external devices (e.g., partially or entirely). More specifically, the wireless communication circuit 129 in the electronics module 120 may include a transmitter and/or receiver (e.g., a transceiver), as well as additional circuitry. For example, the wireless communication circuit 129 may include a Bluetooth chip set (e.g., a Bluetooth Low Energy chip set), a ZigBee chipset, a Thread chipset, etc. As such, the electronics module 120 may wirelessly provide data (e.g., the parameters determined by the controller, such as pressure measurements, temperature, humidity level, inhaler orientation) to an external device, including a smartphone. The external device may include software for processing the received information and for providing compliance and adherence feedback and/or any of the notifications described herein to users of the inhalation device 100 via a graphical user interface (GUI).

Figure 7A:
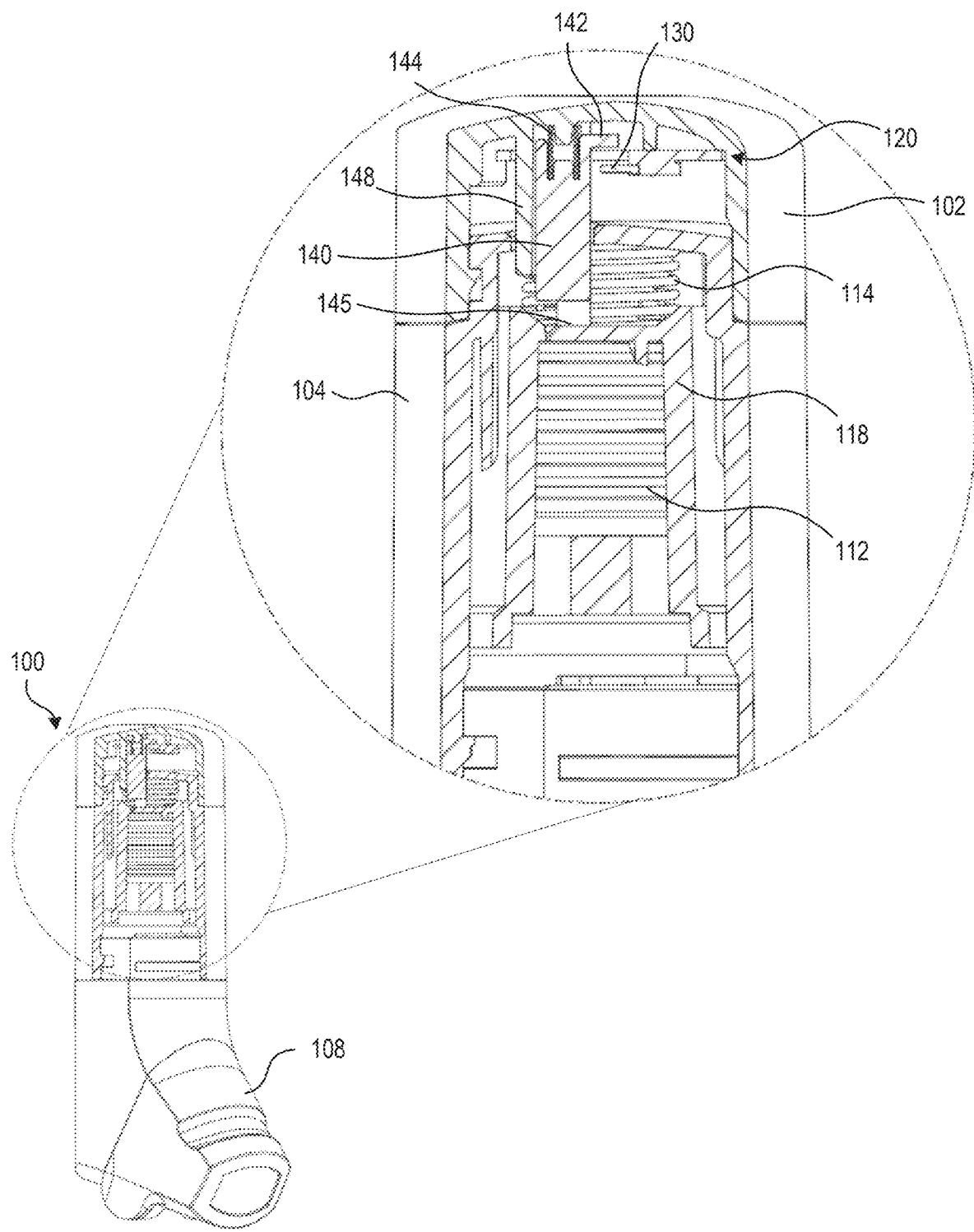
FIG. 7A is a partial cross-sectional view of the inhalation device with a mouthpiece cover of the inhalation device in a closed position.
Figure 7B:
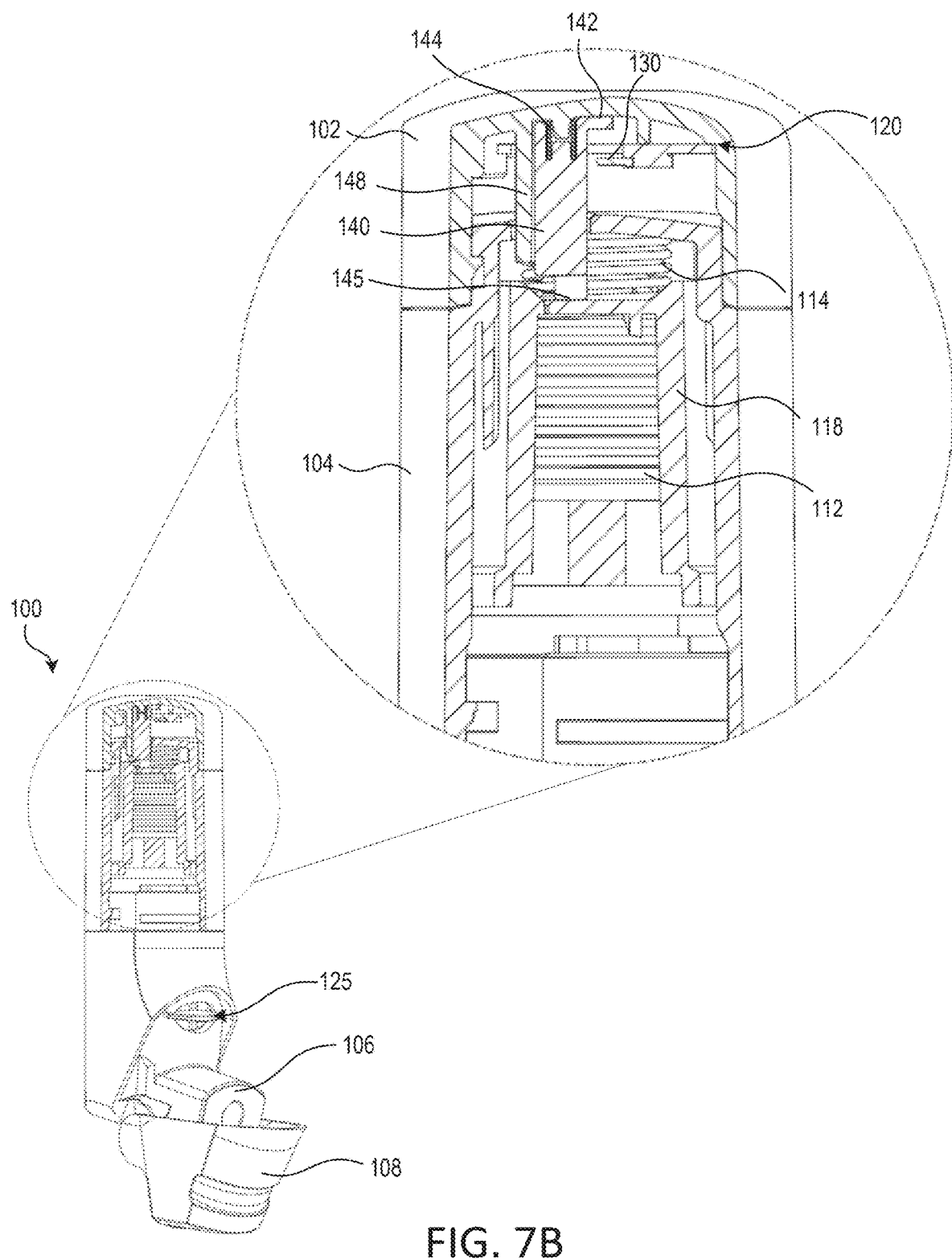
FIG. 7B is a partial cross-sectional view of the inhalation device with the mouthpiece cover in a partially open position.

FIGS. 7A-7D describe an example of the internal operation of the inhalation device 100 as the mouthpiece cover 108 is opened to expose the mouthpiece 106 and to make a dose of medication available to the flow pathway 119. It should be appreciated that other examples of the inhalation device 100 may include a subset of the actions described herein. Referring to FIG. 7A, the distal end 145 of the slider 140 may be configured to abut the yoke 118 that resides within the main housing 104. When the mouthpiece cover 108 is in the closed position, the arm 142 of the slider 140 may not be in contact with the switch 130. Further, the slider spring 144 and the bellows spring 114 may be in a compressed state. As the mouthpiece cover 108 is opened to expose the mouthpiece 106, the yoke 118 may move upward in the main housing 104, for example, due to a mechanical connection between the yoke 118 and the mouthpiece cover 108. The upward movement of the yoke 118 may cause the slider 140 to move upward within the top cap 102, further compressing the slider spring 144 and the bellows spring 114, for example, as shown in FIG. 7B.

Figure 7C:
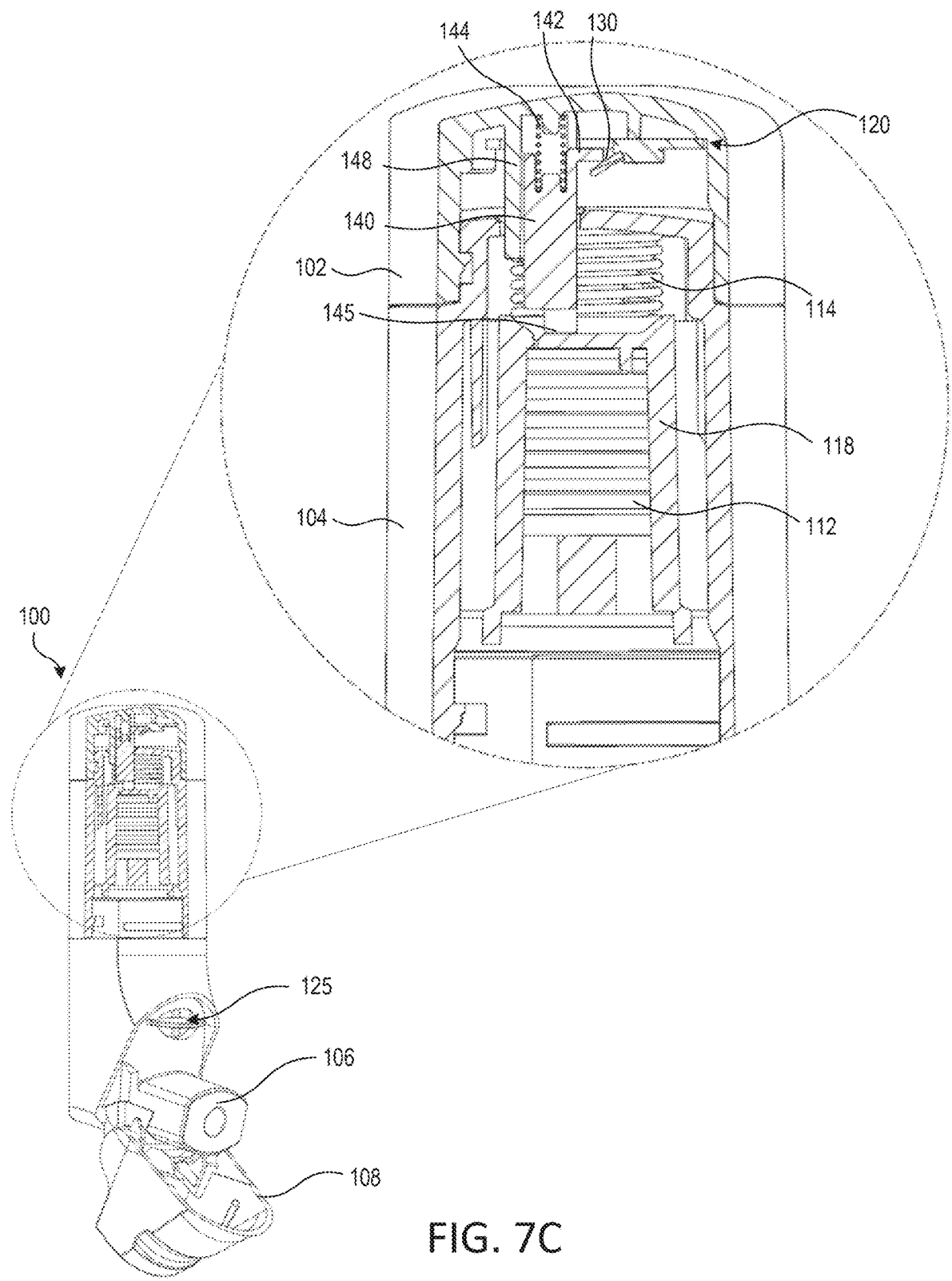
FIG. 7C is a partial cross-sectional view of the inhalation device with the mouthpiece cover in a partially open position.

As the mouthpiece cover 108 continues to move toward the fully open state, for example as shown in FIG. 7C, the mouthpiece cover 108 may cause the yoke 118 to drop within the main housing 104 (e.g., due to the downward force applied by the bellows spring 114). The movement of the yoke 118 may cause the slider 140 to drop (e.g., due to the downward force applied by the slider spring 144), which may cause the arm 142 of the slider 140 to engage the switch 130 and begin to actuate the switch 130. The downward movement of the slider 140 may be limited by the position of the yoke 118 as the distal end 145 of the slider 140 may rest upon the top of the yoke 118.

Figure 7D:
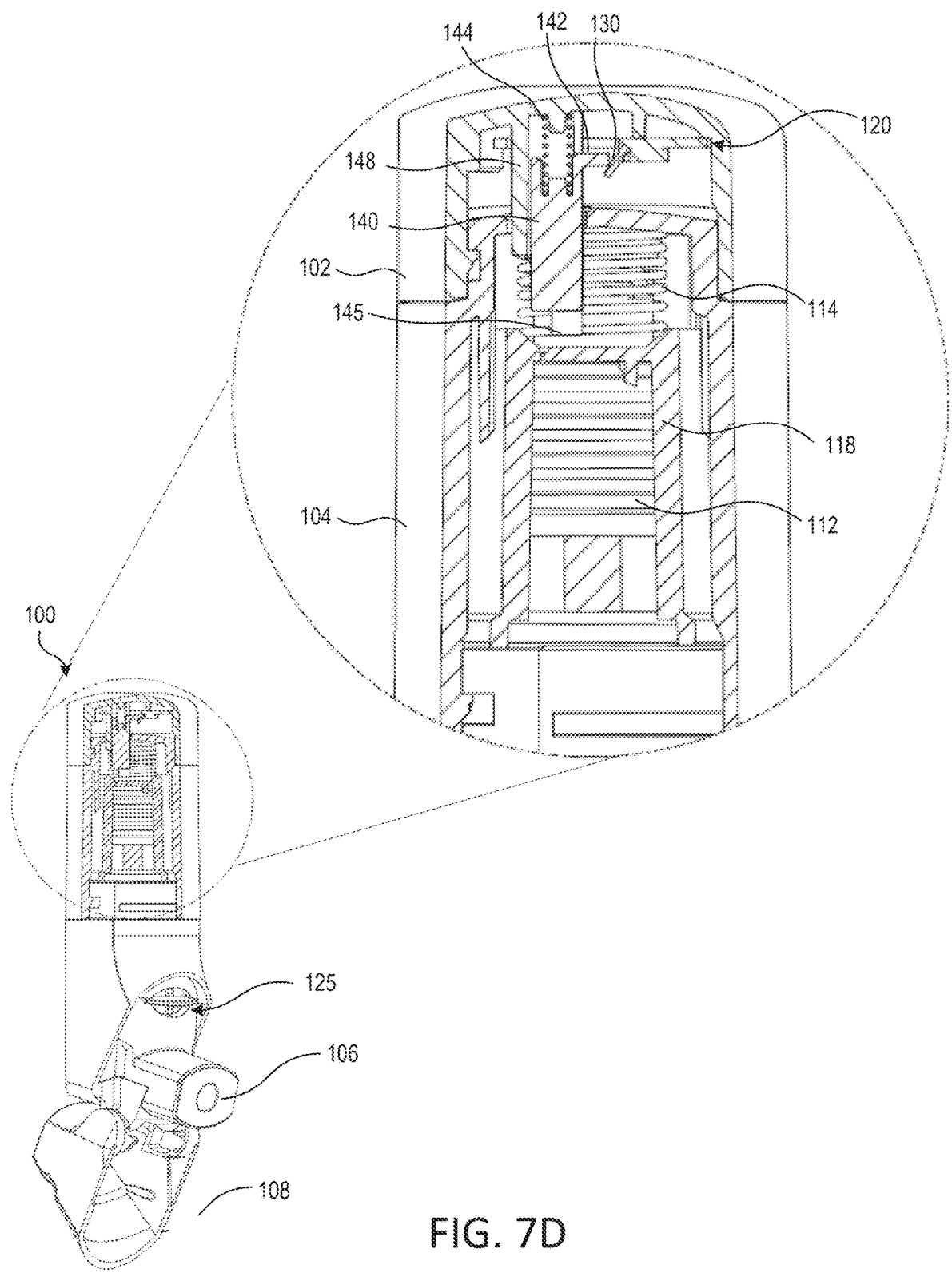
FIG. 7D is a partial cross-sectional view of the inhalation device with the mouthpiece cover in a fully open position.

As the mouthpiece cover 108 continues to open, as shown in FIG. 7D, the arm 142 of the slider 140 may (e.g., fully) actuate the switch 130, which may generate a signal causing the electronics module 120 to change states, such as from an off or sleep state to an active state. Thus, the controller of the electronics module 120 may wake and provide power to the sensor system 128 to enable the sensor system 128 to take measurement readings. Moreover, the movement of the yoke 118 caused by the opening of the mouthpiece cover 108 may also cause the yoke 118 to compress the bellows 112 to cause a dose of medication to be delivered from the medication reservoir 110 to the dosing cup 116, resulting in the medication being made available to the flow channel 119. The medication may be delivered from the dosing cup 116 through the flow channel and out the mouthpiece 106 when a user inhales from the mouthpiece 106. Further, when the mouthpiece cover 108 reaches the fully open position (e.g., as shown in FIG. 7D), the slider 140 may be no longer in contact with the yoke 118 (e.g., the stopper 144 may stop the vertical travel of the slider 140 such that the slider 140 is no longer be in contact with the yoke 118).

The electronics module 120 may have a plurality of power states, each with respective power consumption levels. For example, the electronics module 120 may be configured to operate in a system off state, a sleep state, and/or an active state. While the electronics module 120 is in the active state, the electronics module 120 may operate in one or more modes, such as a measurement mode, a data storage/data processing mode, an advertising mode, and/or a connected mode. It should be appreciated that the electronics module 120 may operate in multiple modes at one time (e.g., the modes may overlap).

In the measurement mode, the controller of the electronics module 120 may power on the sensor system 128. The controller may cause the sensor system 128 to take pressure measurement readings, temperature readings, humidity readings, orientation readings, etc. for a predetermined time period (e.g., up to 60 seconds) and/or until the mouthpiece cover 108 is closed or no changes in pressure are detected. The controller may turn off one or more components of the electronics module 120 while the sensor system 128 is capturing readings to further conserve power. The sensor system 128 may sample the readings at any suitable rate. For example, the sensor system 128 may have a sample rate of 100 Hz and thus a cycle time of 10 milliseconds. The sensor system 128 may generate a measurement complete interrupt after the measurement cycle is complete. The interrupt may wake the controller or cause it to turn on one or more components of the electronics module 120. For example, after or while the sensor system 128 is sampling one or more pressure measurements, temperature readings, humidity readings, orientation readings, etc., the controller may process and/or store the data and, if measurements are complete, power off the sensor system 128.

In some examples, the controller of the electronics module 120 may be configured to cause the temperature and/or humidity sensors to take a single measurement each during the measurement mode, and may cause the orientation sensor to take periodic (e.g., continuous) measurements through the measurement mode. Accordingly, the controller of the electronics module 120 may be configured to record a signal temperature measurement and/or a single humidity measurement in response to the mouthpiece cover 108 being moved from the closed position to the open position, and additionally, the controller of the electronics module 120 may be configured to periodically (e.g., continuously) monitor the orientation of the inhalation device 100 in response to the mouthpiece cover 108 being moved from the closed position to the open position.

In the data storage/data processing mode, the controller may power on at least a portion of the memory within the electronics module 120. The controller may process the readings from the sensor system 128 to compute, estimate, calculate or otherwise determine parameters (e.g., usage and/or storage conditions) and store the parameters in a memory. The controller may also compare the readings and/or parameters to one or more thresholds or ranges to assess how the inhalation device 100 is being used and/or the conditions under which the device 100 is being used. Depending on the results of the comparison, the controller may drive the indicators to provide feedback to the user of the inhalation device 100. As noted above, the electronics module 120 may operate in the measurement mode and the data storage/data processing mode simultaneously.

In the connected mode, the communication circuit and memory may be powered on and the electronics module 120 may be "paired" with an external device, such as a smartphone. The controller may retrieve data from the memory and wirelessly transmit the data to the external device. The controller may retrieve and transmit all of the data currently stored in the memory. The controller may also retrieve and transmit a portion of the data currently stored in the memory. For example, the controller may be able to determine which portions have already been transmitted to the external device and then transmit the portion(s) that have not been previously transmitted. Alternatively, the external device may request specific data from the controller, such as any data that has been collected by the electronics module 120 after a particular time or after the last transmission to the external device. The controller may retrieve the specific data, if any, from the memory and transmit the specific data to the external device.

Further, when connected with the external device, the electronics module 120 may be configured to transmit Bluetooth special interest group (SIG) characteristics for managing access to data stored in the module 120. The Bluetooth SIG characteristics may include one or more of a manufacturer name of the inhalation device 100, a serial number of the inhalation device 100, a hardware revision number of the inhalation device 100, and/or a software revision number of the inhalation device 100. When connected with the external device, the electronics module 120 may retrieve data from memory and transmit the data to the external device.

After determining one or more parameters (e.g., usage and/or storage conditions) from the readings of the sensor system 128, the inhalation device 100 may transmit the parameters and/or associated timestamps (e.g., based on the internal counter) to the external device when in the connected mode. For example, the signals generated by the switch 130, the measurement readings taken by the sensory system 128 may be timestamped and stored in memory. The foregoing parameters may be indicative of various usage and/or storage conditions associated with the inhalation device 100. For example, as movement of the slider 140 causes the switch 130 to transition between "on" and "off", the controller of the electronics module 120 may use the signals from the switch 130 to record and timestamp each transition. Further, as the transition of the switch 130 between "on" and "off" may correlate to the position of the mouthpiece cover 108 (e.g., open or closed), the electronics module 120 may be able to detect and track the position of the mouthpiece cover 108 over time. It will be appreciated that the electronics module 120 may be able to sense and track the status of the mouthpiece cover 108 without interfering with the delivery of medication through the flow pathway 119 of the inhalation device 100.

The inhalation device 100 may include multiple dose counters, such as any combination of one or more mechanical dose counters and/or electrical dose counters. The mechanical dose counter(s) and the electrical dose counter(s) may be triggered to increment or decrement a counted dose (e.g., record a dosing event) based on different actuations or actions occurring at the inhaler. As noted above, the inhalation device 100 may include a mechanical dose counter, such as the dose counter 111, and the reading (e.g., count or number) displayed by the dose counter 111 may be referred to as a mechanical dose reading. A mechanical dose reading may correspond to a dosage count determined by or based on the mechanical dose counter 111. The dose counter 111 may advance (e.g., increment or decrement) each time the mouthpiece cover 108 is opened or each time the mouthpiece cover 108 is closed. Although the mechanical dose counter 111 is described as being actuated based on movement of the mouthpiece cover 108, in other examples, the mechanical dose counter 111 may take other forms and/or be triggered based on other actuations of the inhalation device 100 (e.g., such as the push of a button of the inhalation device 100, the turn of a dial, movement of a lever or switch, etc., which may cause medication to be dispensed or prepared).

The inhalation device may include the electronics module 120 that records dosing events based on, for example, actuations of the inhalation device (e.g., movement of the mouthpiece cover 108, actuations of an internal switch, etc.) and/or based on feedback from the sensor system 128 (e.g., based on measurements from the sensor system 128 indicating a flow rate above a particular threshold). Different sensors may be associated with corresponding criteria or thresholds for determining whether a dosing event has occurred. As a result, different circumstances may result in a recording of a dosing event based on data from a first sensor, but may not result in the recording of a dosing event from a second sensor. When data from a sensor is used by the electronics module of the inhalation device and/or by a processor of the external device to determine whether to record a dosing event, the recorded dosing event may be referred to as an electronic dose reading.

An electronic dose reading may be a dosage count or value that is determined based on instances where the switch 130 is actuated (e.g., based on the signal generated in response to the switch 130 being actuated during an opening of the mouthpiece cover 108). Alternatively or additionally, an electronic dose reading may be a dosage count or value that is determined based on interpreting or processing sensor data from a sensor present on the inhalation device 100. Examples of electronic dose reading data may include a signal received or generated based on the switch 130 being actuated and/or raw or processed data from one or more (or any combination therefore) pressure sensor(s), temperature sensor(s), humidity sensor(s), acoustic sensor(s), optical sensor(s), orientation sensor(s), and/or any other raw or processed data from any sensor of the inhalation device.

One or more electronic dose reading(s)/electronic dosage count(s) from one or more sensor(s) may be compared to one another and/or compared to a mechanical dose reading/mechanical dose count to determine whether there is a discrepancy and/or whether the discrepancy exceeds a threshold. In an example, a first electronic dose reading from a first set of one or more sensor(s) may be compared to a second electronic dose reading from a second set of one or more sensor(s) to determine whether there is a discrepancy and/or whether the discrepancy exceeds a threshold.

For example, the electronics module 120 may include the switch 130 and one or more sensors, such as a pressure sensor. The electronics module 120 may record a dosing event each time the switch 130 is actuated, which for example, may be performed when the mouthpiece cover 130 is moved from the closed position to the open position. For example, each time the switch 130 is activated via the opening of the mouthpiece cover 108, the signal generated by the switch 130 may be counted as a dosing event. Accordingly, the number of actuations of the switch 130 and the number of advancements in the dose counter 111 may yield the same (or at least similar) result in terms of dose tracking. However, in some instances, the number of actuations of the switch 130 and the number of advancements in the dose counter 111 may be different, for example, due to mis-operation of the inhalation device 100 by the user.

The data collected and stored by the electronics module 120 (e.g., the recorded dosing events) may also be used to estimate the number doses that have been delivered from the inhalation device 100 and/or estimate the number of doses that remain in the medication reservoir 110. The inhalation device 100 may be deemed to have delivered 60 doses when the mouthpiece cover 108 is opened 60 times. The inhalation device 100 may be configured to store enough medication in the medication reservoir 110 to deliver a predefined total number of doses, such as a total of 200 doses. As such, the inhalation device 100 may also be deemed to have 140 doses remaining after the mouthpiece cover 108 is opened 60 times.

The electronics module 120 may count doses each time the pressure sensor from the sensor system 128 provides a pressure measurement above a threshold (e.g., 30 liters per minute (L/min)), for example, in addition to or as an alternate to counting doses based on each time the switch 130 is actuated. The electronics module 120 may record (e.g., store in memory) a dosing event each time the sensor system 128 provides a pressure measurement above the threshold. As noted above, medication may not be delivered from the medication reservoir 110 upon the user opening the mouthpiece cover 108 if a previous dose of medication was not properly aerosolized by the deagglomerator 121 and/or transferred from the dosing cup 116. Thus, it will be appreciated that counting the number of doses delivered based on the opening or closing of the mouthpiece cover 108 may not accurately reflect the actual number of doses delivered by the inhalation device 100 if, for example, a user opens and closes the mouthpiece cover 108 without inhaling from the mouthpiece 106.

For example, the deagglomerator 121 in the inhalation device 100 may be configured to (e.g., fully) aerosolize the medication in the dosing cup 116 when the airflow through the flow pathway 119 exceeds a threshold, such as 30 L/min. As such, a dose may be counted as delivered each time the peak airflow measured by the sensor system 128 is above the threshold (e.g., 30 LPM), thereby accounting for circumstances in which the mouthpiece cover 108 was opened but the medication in the dosing cup 116 was only partially aerosolized (or not aerosolized at all) by the deagglomerator 121.

The inhalation device 100 (e.g., the controller of the electronics module 120) and/or a mobile application residing on the external device may be configured to detect a discrepancy between two or more of the dose counters (e.g., any combination of the mechanical and/or electrical dose readings) of the inhalation device 100. The detected discrepancy can be any difference in a detected dosage determined using a first method of detecting dosage and a second method of detecting dosage. The inhalation device 100 and/or the external device (e.g., mobile application) may determine the detected dosages based on the reading displayed by a mechanical dose counter (e.g., the dose counter 111) and/or based on signals based on the actuation of the switch 130 and/or received from one or more the sensors of the inhalation device 100. For example, the inhalation device 100 and/or external device may be configured to detect a discrepancy between the number of doses counted by the dose counter 111 and the number of doses counted by the electronics module 120. Alternatively or additionally, the inhalation device 100 and/or external device may be configured to detect a discrepancy between the number of doses counted based on signals received from two different sensors of the electronics module 120, and/or based on the number of doses counted based on actuations of the switch 130 and signals received from a sensor of the electronics module 120 The discrepancy may be detected as a difference in the number of dose counts. For example, any number and combination of dose counts detection methods may be used, and a difference between any two or more dose count detection methods may be considered a discrepancy.

As an example, a dosing event (e.g., dose count) may be determined using airflow metrics, such as readings from the pressure sensor. A dosing event (e.g., dose count) may be determined based on actuations of the switch 130. A dosing event(s) (e.g., dose count(s)) may be determined based on feedback from another sensor(s), such as a temperature, humidity, and/or orientation sensors of the device. The controller of the electronics module 120 may be configured to track dosing events each time the airflow through the flow pathway 119 exceeds a threshold (e.g., 30 LPM), each time the switch 130 is actuated, and/or based on feedback from one or more other sensors of the inhalation device 100.

The inhalation device 100 (e.g., the controller of the electronics module 120) and/or a mobile application residing on the external device may be configured to identify and provide a notification (e.g., a warning) about inhaler misuse or defect when the discrepancy between the number of doses counted by two or more of the dose counters and/or dose readings exceeds a dose discrepancy threshold (e.g., 5 dose discrepancy). For example, the electronics module 120 may cause an LED may illuminate, change color, and/or flash if the discrepancy exceeds of the dose discrepancy threshold. Alternative or additionally, the mobile application may provide a notification if the discrepancy exceeds of the dose discrepancy threshold. Further, the mobile application may prompt the user to call the customer service center and/or play a video explaining the directions for use of the inhalation device 100 if the discrepancy exceeds the dose discrepancy threshold. Further, the inhalation device 100 (e.g., the controller of the electronics module 120) and/or a mobile application residing on the external device may be configured to identify and provide a notification about inhaler misuse or defect to the user when the difference between the dosing events (e.g., based on actuations of the switch 130 or based on a mechanical dose reading) and the inhalation events (e.g., based on feedback from one or more sensors of the electronics module 120) exceeds the dose discrepancy threshold.

For example, the inhalation device 100 and/or a mobile application residing on the external device may provide a notification that is specific to the type of discrepancy. The notification may be provided to the user, manufacturer of the inhaler, or a HCP. For example, if the discrepancy indicates that the user has operated the mouthpiece cover (e.g., or operated another mechanical actuation component of the inhalation device 100) a greater number of times than the user has inhaled through the inhalation device (e.g., based on feedback from the one or more sensors of the inhalation device 100), the notification may notify the user, manufacturer of the inhaler, or a HCP that the user is not inhaling each time the inhalation device 100 is actuated (e.g., or not inhaling strong enough based on multiple low or no inhalation events, in which case the notification may instruct the user how to properly inhale). Further, if the discrepancy indicates that the user has operated the mouthpiece cover (e.g., or operated another mechanical actuation component of the inhalation device 100) a greater number of times than the switch 130 has been actuated, then the notification may indicate that there is a malfunction with the connection between the dose delivery mechanism and switch 130 of the electronics module (e.g., a mechanical break, an electrical failure, such as due to water damage, etc.). If the discrepancy indicates that the user has operated the mouthpiece cover (e.g., or operated another mechanical actuation component of the inhalation device 100) a fewer number of times than an electronic dose reading (e.g., based on the switch 130 being actuated and/or sensor data), the notification may indicate that there may be a failure with the mechanical dose counter 111 and/or dose delivery mechanism.

More generally, there may be expected relationships between sensor data based on use of the inhaler, and difference thresholds may be established between data from two or more sensors for determining whether a discrepancy has occurred and what is the cause of the error. Therefore, the thresholds values for differences in readings between data from two different sensors may be specific to those two sensors. As an example, there may be a discrepancy threshold value specific to the readings from a pressure sensor and an acoustic sensor. The discrepancy threshold value specific to the readings from a pressure sensor and an acoustic sensor may be different that the is a discrepancy threshold value specific to the readings from a pressure sensor and an mechanical sensor. Notifications may be provided based on the sensor specific discrepancy threshold value that was exceeded. Exceeding different sensor specific discrepancy threshold values may be interpreted to be different types of events or errors. For example, discrepancy between the data from a pressure sensor and an acoustic sensor, (e.g., that exceeds a first sensor-to-sensor threshold) may trigger a notification indicating a failure has occurred with one or more of the sensors. In another example, a discrepancy between the data from a pressure sensor and an mechanical sensor, (e.g., that exceeds a second sensor-to-sensor threshold) may trigger a notification indicating that the patient is not inhaling properly.

The inhalation device 100 may communicate (e.g., wirelessly communicate) individual dosing events, raw sensor data, and/or the number of doses counted by the electronics module 120 to the external device (e.g., to the mobile application residing on the external device). For instance, the electronics module 120 may determine one or more electronic dose readings (e.g., based on actuations of the switch 130 and/or feedback from one or more sensors) or the electronics module 120 may store dosing events (based on actuations of the switch 130 and/or feedback from one or more sensors, such as when this feedback exceeds a threshold) and/or raw sensor data in memory and send the dosing events and/or raw sensor data to the external device, and the external device may calculate the electronic dose reading(s). The external device may determine a mechanical dose reading (e.g., the number of doses counted by the dose counter 111) by, for example, prompting the user or a technician to manually input the number of doses into the mobile application, through the use of a camera of the external device (e.g., by prompting the user to take a picture of the dose counter 111 or hold the camera over the dose counter 111), and/or the like.

Determining when the discrepancy between the number of doses counted by the dose counter 111 and the number of doses counted by the electronics module 120 exceeds the dose discrepancy threshold may be useful in verifying clinical trial results, detecting abnormal patient usage, detecting device failure, etc. The discrepancy may be due, for example, to the user not fully opening and/or closing the mouthpiece cover 130 prior to or after a use of the inhalation device 100. The discrepancy may be due, for example, to the user not properly inhaling a dose of medication (e.g., not inhaling with enough force to cause the dose of medication to leave the inhalation device 100 and enter the user's lungs).

The dose discrepancy threshold may be variable throughout the life of the inhalation device 100. There may be a natural mechanical error rate associated with the dose counter 111 that is determined over the life of the inhalation device 100. For instance, the dose counter 111 may have an error rate of +/−5 doses during the course of the administration of the full 200 doses of the medication reservoir 200. That is, assuming proper use of the inhalation device 100, the dose counter 111 may be off at most +/−5 doses during the course of the administration of a full 200 doses. Similarly, there may be an error rate associated with the airflow metric measurements performed by the electronics module 120. Since the error rates are determined based on the administration of the full capacity of the medication reservoir 110, the dose discrepancy threshold may be variable based on the number of doses remaining in the medication reservoir. Accordingly, the dose discrepancy threshold may change based on the number of doses remaining in the medication reservoir 110.

The dose discrepancy threshold may increase linearly or logarithmically as the estimated remaining doses in the medication reservoir 110 decreases. For example, the dose discrepancy threshold may be a first value (e.g., 2 doses) when the electronics module 120 estimates that number of doses remaining in the medication reservoir 110 is in a first range (e.g., between 200 and 150 doses remaining), a second value (e.g., 4 doses) when the estimated remaining doses is in a second range (between 150 and 50 doses remaining), and a third value (e.g., 5 doses) when the estimated remaining doses is in a third range (less than 50 doses remaining).

The data stored in the memory of the electronics module 120 (e.g., the signals generated by the switch 130, the measurement readings taken by the sensor system 128 and/or the parameters computed by the controller of the electronics module 120) may be transmitted to an external device, which may process and analyze the data to determine the usage parameters associated with the inhalation device 100. Further, a mobile application residing on the external device may generate feedback for the user based on data received from the electronics module 120. For example, the mobile application may generate daily, weekly, or monthly report, provide confirmation of error events or notifications, provide instructive feedback to the user, and/or the like.

The inhalation device 100 and/or the external device (e.g., via a mobile application residing on the external device) may be configured to provide a notification to the user based on the user's usage of the inhalation device 100. For example, the inhalation device 100 and/or the external device (e.g., via a mobile application residing on the external device) may provide a notification based on a pouch related event (e.g., out-of-pouch event, the time out of pouch, etc.), based on a discrepancy detected between two or more dose counter readings (e.g., readings from a mechanical dose counter and an electrical dose counter), based on feedback from the sensor system 128, etc. The notification may be unique to each event. The notification may, for example, be the illumination of an LED, the generation of an audible output via a speaker of the inhalation device 100 or external device, the presentation of a message via the mobile application, the presentation of an error video or the instructions for use, by sending a text, email, or instant message to the external device or DHP, and/or by providing a notification to the DHP.

Figure 9:
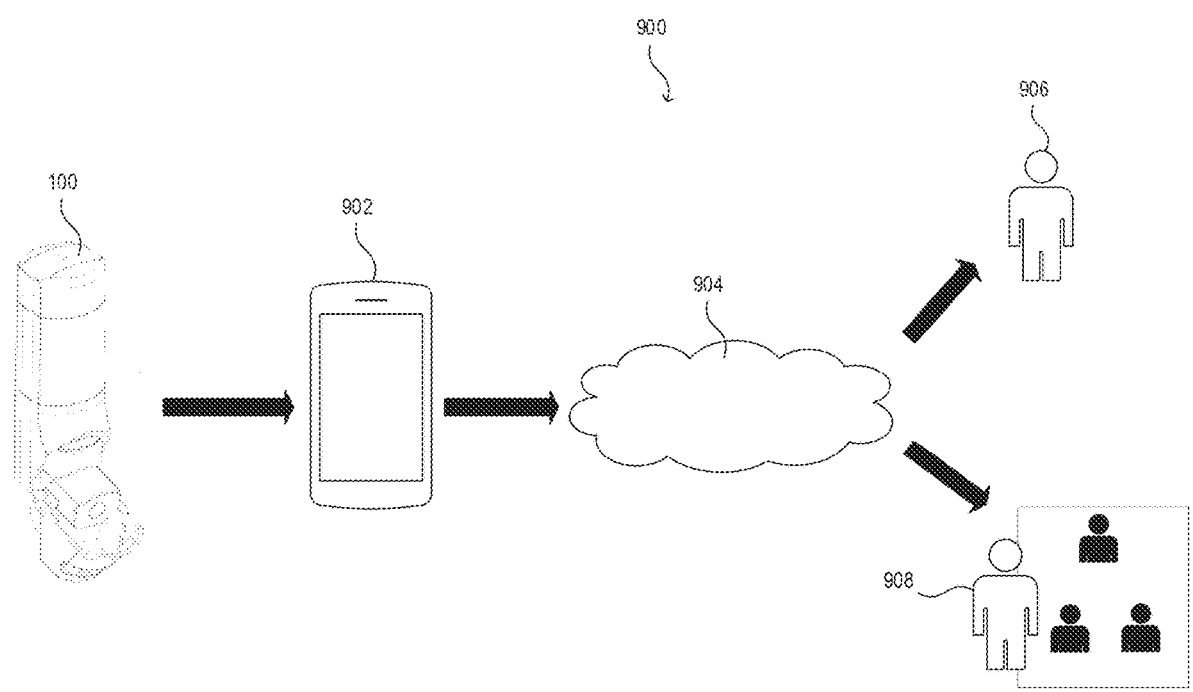
FIG. 9 is a diagram of an example system including the inhalation device.

FIG. 9 is a diagram of an example system 900 including the inhalation device 100, an external device (e.g., a mobile device 902), a public and/or private network 904 (e.g., the Internet, a cloud network), a health care provider 906, and a third party 908 (e.g., friends, family, pharmaceutical manufacturer, etc.). The mobile device 902 may include a smart phone (e.g., an iPhone® smart phone, an Android® smart phone, or a Blackberry® smart phone), a personal computer, a laptop, a wireless-capable media device (e.g., MP3 player, gaming device, television, a media streaming devices (e.g., the Amazon Fire TV, Nexus Player, etc.), etc.), a tablet device (e.g., an iPad® hand-held computing device), a Wi-Fi or wireless-communication-capable television, or any other suitable Internet-Protocol-enabled device. For example, the mobile device 902 may be configured to transmit and/or receive RF signals via a Wi-Fi communication link, a Wi-MAX communications link, a Bluetooth® or Bluetooth Smart communications link, a near field communication (NFC) link, a cellular communications link, a television white space (TVWS) communication link, or any combination thereof. The mobile device 902 may transfer data through the public and/or private network 904 to the health care provider 906 and/or one or more third parties 908 (e.g., friends, family, pharmaceutical company, etc.).

As noted above, the inhalation device 100 may include a communication circuit, such as a Bluetooth radio, for transferring data to the mobile device 902. The data may include the signals generated by the switch 130, the measurement readings taken by the sensor system 128 and/or parameters computed by the controller of the electronics module 120. The inhalation device 100 may receive data from the mobile device 902, such as, for example, program instructions, operating system changes, dosage information, alerts or notifications, acknowledgments, etc.

The mobile device 902 may process and analyze the data to determine the usage parameters associated with the inhalation device 100. For example, the mobile device 902 may process the data to identify no inhalation events, low inhalations events, good inhalation events, excessive inhalation events and/or exhalation events. The mobile device 902 may also process the data to identify underuse events, overuse events and optimal use events. The mobile device 902 may further process the data to estimate the number of doses delivered and/or remaining and to identify error conditions, such as those associated with a timestamp error flag. The mobile device 902 may include a display and software for visually presenting the usage parameters through a GUI on the display.

What is claimed is:

1. A system comprising:
   an inhaler comprising a mouthpiece, medicament, a mechanical dose counter, and an electronics module, the electronics module comprising a processor and a communication circuit;
   wherein the electronics module is configured to record a dosing event, and send a signal associated with the dosing event to an external device; and
   a computer-readable storage medium residing on the external device, wherein the computer-readable storage medium comprises computer-executable instructions that, when executed by a processor of the external device cause the processor of the external device to:
   determine a mechanical dose reading of the mechanical dose counter;
   determine an electronic dose reading based on the signal associated with the dosing event;
   determine that a discrepancy between the mechanical dose reading and the electronic dose reading exceeds a threshold; and
   provide a notification to the user, a manufacturer of the inhaler, or a health care provider (HCP) based on the discrepancy.

2. The system of claim 1, wherein the mechanical dose counter is configured to decrement based on an actuation of the inhaler.

3. The system of claim 1, wherein the inhaler comprises a mouthpiece cover;
   wherein the electronics module is configured to record the dosing event when the mouthpiece cover is moved from a closed position to an open position to expose the mouthpiece; and
   wherein the mechanical dose counter is configured to decrement when the mouthpiece cover is moved from the open position to the closed position to cover the mouthpiece.

4. The system of claim 1, wherein the inhaler further comprises a sensor configured to measure air flow through the inhaler, and wherein the electronics module is configured to record the dosing event when a measurement from the sensor indicates a flow rate that exceeds a threshold.

5. The system of claim 1, wherein, when executed by the processor of the external device, the computer-readable storage medium is configured to cause the processor of the external device to prompt the user or a technician of the manufacturer to input the mechanical dose reading into the external device to determine the mechanical dose reading.

6. The system of claim 1, wherein, when executed by the processor of the external device, the computer-readable storage medium is configured to cause the processor of the external device to use a camera of the external device to determine the mechanical dose reading.

7. The system of claim 1, wherein, when executed by the processor of the external device, the computer-readable storage medium is configured to cause the processor of the external device to decrement the electronic dose reading for each signal associated with the dosing event that is received from the electronics module.

8. The system of claim 1, wherein the electronics module is configured to determine the electronic dose reading based on recorded dosing events, and send the electronic dose reading to the external device.

9. The system of claim 1, wherein, when executed by the processor of the external device, the computer-readable storage medium is configured to cause the processor of the external device to provide the notification to the user by way of a mobile application residing on the external device, by illuminating one or more light emitting diodes (LEDs) of the inhaler, or by outputting an audible signal through a speaker of the inhaler or the external device.

10. The system of claim 1, wherein the inhaler further comprises a sensor configured to measure a characteristic of inhalation through the inhaler, and a switch configured to change a power state of the electronics module;
wherein the electronics module is configured to record a first dosing event based feedback from the sensor and a second dosing event based on actuation of the switch;
wherein, when executed by the processor of the external device, the computer-readable storage medium is configured to cause the processor of the external device to provide a first notification that is specific to discrepancy between the mechanical dose reading and an electronic dose reading that is calculated using the first dosing event, and provide a second notification that is specific to discrepancy between the mechanical dose reading and an electronic dose reading that is calculated using the second dosing event.

11. A system comprising:
an inhaler comprising a mouthpiece, a mouthpiece cover, and an electronics module, the electronics module comprising a processor, a switch, a sensor, and a communication circuit;
wherein the electronics module is configured to:
record a dosing event in response to actuation of the switch;
record an inhalation event in response to a measurement from the sensor exceeding a threshold indicative of an inhalation during an inhalation by the user via the mouthpiece of the inhaler; and
send a signal indicating the dosing event and the inhalation event to an external device; and
a computer-readable storage medium residing on the external device, wherein the computer-readable storage medium comprises computer-executable instructions that, when executed by a processor of the external device, cause the processor of the external device to:
determine that a discrepancy between a number of dosing events of the inhaler and a number of inhalation events of the inhaler exceeds a threshold; and
provide a notification to the user, a manufacturer of the inhaler, or a health care provider (HCP) based on the discrepancy.

12. The system of claim 11, wherein the inhaler further comprises a bellows and a dosing cup; and
wherein the mouthpiece cover moving from the closed position to the open position causes the bellows to compress to deliver the dose of medicament from a medicament reservoir to the dosing cup to prepare the dose of medicament for inhalation by the user.

13. The system of claim 11, wherein the switch is configured to be actuated in response to the mouthpiece cover of the inhaler being moved from a closed position to an open position to expose the mouthpiece.

14. The system of claim 11, wherein the mouthpiece cover moving from the closed position to the open position causes a dose of medicament to be prepared for inhalation by the user.

15. The system of claim 11, wherein, when executed by the processor of the external device, the computer-readable storage medium is configured to cause the processor of the external device to generate a notification that prompts the user or a technician of the manufacturer to enter a mechanical dose reading into the external device to determine the mechanical dose reading.

16. The system of claim 14, wherein, when executed by the processor of the external device, the computer-readable storage medium is configured to cause the processor of the external device to prompt the user to use a camera of the external device to determine a mechanical dose reading.

17. A system comprising:
an inhaler comprising a mouthpiece, a mechanical dose counter, and an electronics module, wherein the electronics module comprises a processor, a sensor, and a communication circuit;
wherein the electronics module is configured to:
record an inhalation event in response to a measurement from the sensor exceeding a threshold indicative of an inhalation during an inhalation by the user via the mouthpiece of the inhaler; and
send a signal indicating the inhalation event to an external device; and
a computer-readable storage medium residing on the external device, wherein the computer-readable storage medium comprises computer-executable instructions that, when executed by a processor of the external device, cause the processor of the external device to:
determine a mechanical dose reading of the mechanical dose counter;
determine that a discrepancy between the mechanical dose reading and a number of inhalation events exceeds a threshold; and
provide a notification to the user, a manufacturer of the inhaler, or a health care provider (HCP) based on the discrepancy.

18. The system of claim 17, wherein the sensor is configured to measure air flow through the inhaler, and wherein the electronics module is configured to record the inhalation event when the measurement from the sensor indicates a flow rate that exceeds the threshold.

19. The system of claim 17, wherein, when executed by the processor of the external device, the computer-readable storage medium is configured to cause the processor of the external device to prompt the user or a technician of the manufacturer to enter the mechanical dose reading into the external device to determine the mechanical dose reading.

20. The system of claim 17, wherein, when executed by the processor of the external device, the computer-readable storage medium is configured to cause the processor of the external device to provide the notification to the user by way of a mobile application residing on the external device, by illuminating one or more light emitting diodes (LEDs) of the inhaler, or by outputting an audible signal through a speaker of the inhaler or the external device.

\* \* \* \* \*